United States Patent [19]

Burk

[11] Patent Number: 5,426,223
[45] Date of Patent: Jun. 20, 1995

[54] PREPARATION OF OPTICALLY ACTIVE HYDRAZINES AND AMINES

[75] Inventor: Mark J. Burk, Hockessin, Del.

[73] Assignee: E. I. du Pont Nemours and Company, Wilmington, Del.

[21] Appl. No.: 96,571

[22] Filed: Jul. 30, 1993

Related U.S. Application Data

[62] Division of Ser. No. 852,592, Mar. 17, 1992, Pat. No. 5,250,731.

[51] Int. Cl.$^6$ ............................................. C07C 243/14
[52] U.S. Cl. .................... 564/150; 556/419; 560/169; 564/148; 564/149; 568/12
[58] Field of Search ............... 564/148, 149, 150, 151; 556/419; 560/169; 568/12

[56] References Cited

U.S. PATENT DOCUMENTS 5,008,457  4/1691  Burk ...................................... 568/12

OTHER PUBLICATIONS

Baumgarten et al., *J. Org. Chem.*, 41 (24), 3806 (1976).
Harada, K., *Asymmetric Synthesis*, vol. 5, Academic Press, Orlando, FL 360 (1985).
Becalski et al., *Inorg. Chem.*, 30, 5002–5008 (1991).
Bakos et al., *J. Chem. Soc. Chem. Commun.*, 1684 (1991).
Kang et al., *J. Chem. Soc. Chem. Commun.*, 1466 (1988).
Cullen et al., *J. Molecular Catalysis*, 62, 243–253 (1990).
Char. et al., *J. Am. Chem. Soc.*, 112, 9400 (1990).
Spindler et al., *Angew. Chem. Int. Ed. Engl.*, 29, 558 (1990).
Souppe et al., *J. Organometallic Chem.*, 250, 227–236 (1983).
Burk et al., *Organometallics*, vol. 9, 2653–2655 (1990).
Burk et al. *Angew Chem. Int. Ed. Engl.*, 29, 1462–1464 (1990).
Burk et al. *Tetrahedron: Asymmetry*, 2, 569–592 (1991).
Burk, *J. Am. Chem. Soc.*, 113, 8518–8519 (1991).

*Primary Examiner*—Shailendra Kumar

[57] ABSTRACT

A process for the asymmetric hydrogenation of N-acylhydrazones to optically active N-acylhydrazines in the presence of a chiral phospholane catalyst complex, a process for the reductive N—N bond cleavage of N-acylhydrazine to amines with samarium diiodide, and a multistep process for converting keto group-bearing compounds to the corresponding optically active amino group-bearing compounds are disclosed.

17 Claims, No Drawings

PREPARATION OF OPTICALLY ACTIVE HYDRAZINES AND AMINES

This is a division of application Ser. No. 07/852,592, filed Mar. 17, 1992, now U.S. Pat. No. 5,250,731.

FIELD OF THE INVENTION

This invention provides a process for the asymmetric hydrogenation of N-acylhydrazones to optically active N-acylhydrazines. This invention also provides a process for the reductive N—N bond cleavage of N-acylhydrazines to amines. This invention also provides a multistep reductive amination process for the conversion of keto group-bearing compounds to corresponding chiral amino group-bearing compounds.

BACKGROUND OF THE INVENTION

In contrast to the high enantioselectivities observed in certain catalytic olefin (C=C bond) and ketone (C=O bond) hydrogenations, little success has been achieved in the catalytic asymmetric hydrogenation of the C=N bond. The limited success that has been reported is mostly involved with the reduction of imines.

H. E. Baumgarten et al., *J. Org. Chem.*, 41(24), 3806 (1976), disclose the catalytic hydrogenation of N-1-phenylethyl-N'-carbo-tert-butoxyhydrazone to N-1-phenylethyl-N'-carbo-tert-butoxyhydrazine. It is stated that this is a general procedure but that it cannot be used for optically active hydrazines because the reductions are not stereoselective.

K. Harada, Asymmetric Synthesis, Volume 5, Academic Press, 1985, p. 360 describes the hydrogenation of optically active hydrazones to optically active amines. There is no disclosure nor suggestion of a method to generate optically active products from non-optically active starting materials.

J. Souppe et al., *J. Organometallic Chemistry*, 250, 237–236 (1983) report the reductive cleavage of the N—N bond in 1,2-diphenyl hydrazine by samarium diiodide to yield aniline in 55% yield after a 4 day reaction period. There is no disclosure concerning the reactivity of samarium diiodide with N-acylhydrazines.

The present invention provides processes for the asymmetric hydrogenation of N-acylhydrazones to optically active N-acylhydrazines, and the reductive amination of keto group-bearing compounds to corresponding chiral amino group-bearing compounds. The use of transition metal catalysts bearing chiral ligands in these processes provides products in optically active form. The present invention also provides a process for the reductive N—N bond cleavage of N-acylhydrazines.

SUMMARY OF THE INVENTION

The present invention comprises a process for the asymmetric hydrogenation of N-acylhydrazones comprising reacting with hydrogen a compound of formula (2)

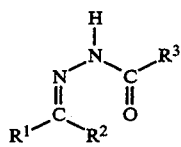

(2)

wherein $R^1$ and $R^2$ are not the same and are each $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroalkyl; aryl; substituted aryl; aralkyl; ring substituted aralkyl; carboalkoxy; carboamido; acyl; vinyl; substituted vinyl; alkynyl; or $C(R^4)_2[C(R^4)_2]_qD[C(R^4)_2]_pR^4$;

D is O, S, $NR^4$ or $Si(R^4)_2$;

p and q are each integers, the same or different, from 1 to 8;

$R^4$ is each independently H; F; aryl; $C_1$ to $C_8$ alkyl; $C_1$ to $C_8$ fluoroalkyl; to $C_1$ to $C_8$ perfluoroalkyl; or $R^4$ together with $R^1$ or $R^2$ form a ring; and $R^3$ is aryl, substituted aryl, or a linear, branched or cyclic $C_1$ to $C_8$ alkyl;

in the presence of a catalyst comprising a complex wherein a transition metal is bonded to both phosphorus atoms of a chiral ligand selected from the group consisting of:

(S)-(−)-2,2'-bis(diphenylphosphino)-1,1'-binaphthyl;
(R)-(+)-2,2'-bis(diphenylphosphino)-1,1'-binaphthyl;
(2S,4S)-2,4-bis(diphenylphosphino)pentane;
(2R,4R)-2,4-bis(diphenylphosphino)pentane;
(2S,3S)-bis(diphenylphosphino)butane;
(2R,3R)-bis(diphenylphosphino)butane;
(+)-2,3-O-isopropylidene-2,3-dihydroxy-1,4-bis(diphenylphosphino)butane;
(−)-2,3-O-isopropylidene-2,3-dihydroxy-1,4-bis(diphenylphosphino)butane;
phenyl-4,6-O-(R)-benzylidene-2,3-O-bis(diphenylphosphino)-β-D-glucopyranoside;
phenyl-4,6-O-(S)-benzylidene-2,3-O-bis(diphenylphosphino)-β-D-glucopyranoside;

a chiral ligand of formulae I and II

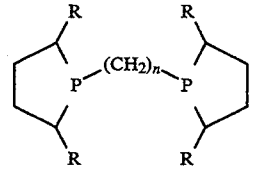

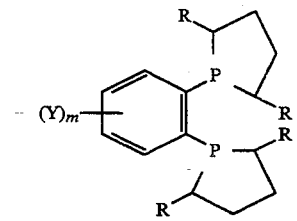

wherein
n is an integer from 1 to 12;
Y is each independently hydrogen, halogen, alkyl, alkoxy, aryl, aryloxy, nitro, dialkylamino, vinyl, substituted vinyl, alkynyl, of sulfonic acid;
m is an integer from 1 to 4;
R is a radical comprising linear, branched or cyclic $C_1$ to $C_8$ alkyl; linear, branched or cyclic $C_1$ to $C_8$ fluoroalkyl; linear, branched or cyclic $C_1$ to $C_8$ perfluoroalkyl; aryl; substituted aryl; aralkyl; ring-substituted aralkyl; or $—C(R^5)_2[C(R^5)_2]_qX[C(R^5)_2]_pR^5$;
X is O, S, $NR^6$, $PR^6$, $AsR^6$, $SbR^6$, divalent aryl, divalent fused aryl, divalent 6-membered ring heterocyclic group, divalent 5-membered ring heterocyclic group, or divalent fused heterocyclic group;

$R^5$ is each independently H; F; aryl; $C_1$ to $C_8$ alkyl; $C_1$ to $C_8$ fluoroalkyl; or $C_1$ to $C_8$ perfluoroalkyl; or where together $R^5$ and $R^6$ form a ring;

q and p are as defined above;

$R^6$ is hydrogen; $C_1$ to $C_8$ alkyl; $C_1$ to $C_8$ fluoroalkyl; $C_1$ to $C_8$ perfluoroalkyl; aryl; substituted aryl; aralkyl; ring substituted aralkyl; or $C(R^5)_2[C(R^5)_2]_qZ[C(R^5)_2]_pR^5$;

Z is O, S, $NR^5$, $PR^5$, $AsR^5$, or $SbR^5$;

$R^5$, p and q are as defined above; and provided that the catalyst is other than ruthenium (2,2'-bis(diphenylphosphino)-1,1'-binaphthyl)dichloride dimer or bis-(2-methylallyl)ruthenium ((2S,5S)-2,5-dimethylphospholano)benzene;

to yield an optically active mixture of enantiomeric N-acylhydrazines of formula (3A) and (3B)

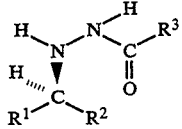

(3A)

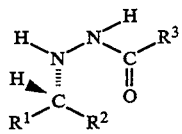

(3B)

wherein $R^1$, $R^2$ and $R^3$ are as defined above.

The present invention further comprises a process for the preparation of amines comprising reacting an N-acylhydrazine of formula (3)

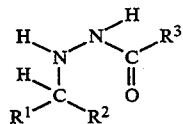

(3)

wherein $R^1$ and $R^2$ are the same or different and are each hydrogen, $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroalkyl; aryl; substituted aryl; aralkyl; ring substituted aralkyl; carboalkoxy; carboamido; acyl; vinyl; substituted vinyl; alkynyl; or $C(R^4)_2[C(R^4)_2]_qD[C(R^4)_2]_pR^4$;

D is O, S, $NR^4$, or $Si(R^4)_2$;

p and q are each integers, the same or different, from 1 to 8;

$R^4$ is H; F; aryl; $C_1$ to $C_8$ alkyl; $C_1$ to $C_8$ fluoroalkyl; to $C_1$ to $C_8$ perfluoroalkyl; or $R^4$ together with $R^1$ or $R^2$ form a ring; and $R^3$ is aryl, substituted aryl, or a linear, branched or cyclic $C_1$ to $C_8$ alkyl;

with samarium diiodide to reductively cleave the nitrogen-nitrogen bond to generate a carboxylic amide of formula $R^3C(O)NH_2$ and an amine of formula (4)

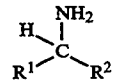

(4)

wherein $R^1$, $R^2$, and $R^3$ are as previously defined.

The present invention further comprises a multistep process for the conversion of prochiral keto group-bearing compounds to the corresponding chiral amino group-bearing compounds comprising Step 1) reacting a ketone of formula $R^1C(O)R^2$ with a carboxylic acid hydrazide of formula $R^3C(O)NHNH_2$ in the presence of an acid catalyst to generate an N-acylhydrazone of formula (2)

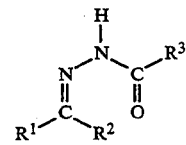

(2)

wherein $R^1$, $R^2$ and $R^3$ are as defined above;

Step 2) reacting the N-acylhydrazone of formula (2) with hydrogen in the presence of a catalyst comprising a complex wherein a transition metal is bonded to both phosphorus atoms of a chiral ligand selected from the group consisting of:

(S)-(−)-2,2'-bis(diphenylphosphino)-1,1'-binaphthyl;
(R)-(+)-2,2'-bis(diphenylphosphino)-1,1'-binaphthyl;
(2S,4S)-2,4-bis(diphenylphosphino)pentane;
(2R,4R)-2,4-bis(diphenylphosphino)pentane;
(2S,3S)-bis(diphenylphosphino)butane;
(2R,3R)-bis(diphenylphosphino)butane;
(+)-2,3-O-isopropylidene-2,3-dihydroxy-1,4-bis(diphenylphosphino)butane;
(−)-2,3-O-isopropylidene-2,3-dihydroxy-1,4-bis(diphenylphosphino)butane;
phenyl-4,6-O-(R)-benzylidene-2,3-O-bis(di-phenylphosphino)-β-D-glucopyranoside;
phenyl-4,6-O-(S)-benzylidene-2,3-O-bis(di-phenylphosphino)-β-D-glucopyranoside;

a chiral ligand of formulae I and II

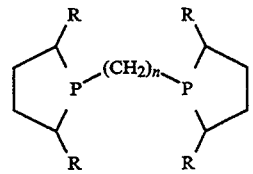

(I)

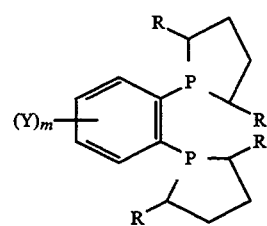

(II)

wherein n is an integer from 1 to 12;

Y is each independently hydrogen, halogen, alkyl, alkoxy, aryl, aryloxy, nitro, dialkylamino, vinyl, substituted vinyl, alkynyl, of sulfonic acid;

m is an integer from 1 to 4;

R is a radical comprising linear, branched or cyclic $C_1$ to $C_8$ alkyl; linear, branched or cyclic $C_1$ to $C_8$ fluoroalkyl; linear, branched or cyclic $C_1$ to $C_8$ perfluoroalkyl; aryl; substituted aryl; aralkyl; ring-substituted aralkyl; or $-C(R^5)_2[C(R^5)_2]_qX[C(R^5)_2]_pR^5$;

X is O, S, $NR^6$, $PR^6$, $AsR^6$, $SbR^6$, divalent aryl, divalent fused aryl, divalent 6-membered ring heterocyclic group, divalent 5-membered ring heterocyclic group, or divalent fused heterocyclic group;

$R^5$ is each independently H; F; aryl; $C_1$ to $C_8$ alkyl; $C_1$ to $C_8$ fluoroalkyl; or $C_1$ to $C_8$ perfluoroalkyl; or where together $R^5$ and $R^6$ form a ring;

q and p are as defined above;

$R^6$ is hydrogen; $C_1$ to $C_8$ alkyl; $C_1$ to $C_8$ fluoroalkyl; $C_1$ to $C_8$ perfluoroalkyl; aryl; substituted aryl; aralkyl; ring substituted aralkyl; or $C(R^5)_2[C(R^5)_2]_qZ[C(R^5)_2]_pR^5$;

Z is O, S, $NR^5$, $PR^5$, $AsR^5$, or $SbR^5$;

$R^5$, p and q are as defined above; and provided that the catalyst is other than ruthenium (2,2'-bis(diphenylphosphino)-1,1'-binaphthyl)dichloride dimer or bis-(2-methylallyl)ruthenium ((2S,5S)-2,5-dimethylphospholano)benzene;

to yield an optically active mixture of enantiomeric N-acyl-hydrazines of formula (3A) and (3B)

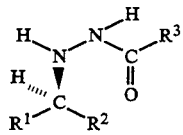   (3A)

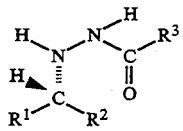   (3B)

wherein $R^1$, $R^2$ and $R^3$ are as previously defined; and

Step 3) reacting the optically active mixture of enantiomeric N-acylhydrazines of formula (3A) and (3B) with samarium diiodide to yield a carboxylic amide of formula (5) $R^3C(O)NH_2$ and an optically active mixture of enantiomeric amines of formula (4A) and (4B)

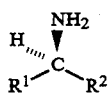   (4A)

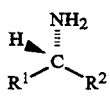   (4B)

wherein $R^1$, $R^2$ and $R^3$ are as previously defined.

The present invention further comprises an optically active N-acylhydrazine of formula (3A) or (3B), or a mixture thereof,

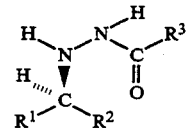   (3A)

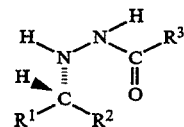   (3B)

wherein $R^1$ and $R^2$ are not the same and are each $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroalkyl; aryl; substituted aryl; aralkyl; ring substituted aralkyl; carboalkoxy; carboamido; acyl; vinyl; substituted vinyl; alkynyl; or $C(R^4)_2[C(R^4)_2]_qD[C(R^4)_2]_pR^4$;

D is O, S, $NR^4$, or $Si(R^4)_2$;

p and q are each integers, the same or different, from 1 to 8;

$R^4$ is each independently H; F; aryl; $C_1$ to $C_8$ alkyl; $C_1$ to $C_8$ fluoroalkyl; to $C_1$ to $C_8$ perfluoroalkyl; or $R^4$ together with $R^1$ or $R^2$ form a ring; and $R^3$ is aryl, substituted aryl, or a linear, branched or cyclic $C_1$ to $C_8$ alkyl.

DETAILED DESCRIPTION OF THE INVENTION

For the purpose of this application, by a "compound with an elevated degree of enantiomeric purity" or a "compound of elevated enantiomeric purity" is meant a compound that exhibits optical activity to the extent of from greater than or equal to about 5% enantiomeric excess (abbreviated ee) up to about 50% ee. By a "compound with a moderately elevated degree of enantiomeric purity", or a "compound of moderately elevated enantiomeric purity" is meant a compound that exhibits optical activity to the extent of greater than or equal to about 50%, enantiomeric excess. By a "compound with a high degree of enantiomeric purity", or a "compound of high enantiomeric purity" is meant a compound that exhibits optical activity to the extent of greater than or equal to about 90%, preferably, greater than or equal to about 95% enantiomeric excess.

Enantiomeric excess is defined as the absolute value arising from the ratio (% R−% S)/(% R+% S) or (% S−% R)/(% S+% R) where % R is the percentage of R enantiomer and % S is the percentage of S enantiomer in a sample of optically active compound.

The ability to enantioselectively hydrogenate the C=N double bonds in N-acylhydrazones has been found to be a key step in a multistep procedure for transforming a compound containing a prochiral keto group into a compound containing an amino group bound at a chiral carbon atom.

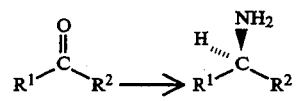

The ability to carry out this conversion has significant commercial value since optically active amino functional group containing compounds are biologically important and have many agricultural and pharmaceutical applications. The value of the conversion rises with an increase of the enantiomeric excess obtained in the product. Carrying out the conversion to yield a compound with an elevated degree of enantiomeric purity is commercially valuable. Carrying out the conversion to yield a compound of moderately elevated enantiomeric excess or a high degree of enantiomeric excess can be extremely valuable. Prior to this invention, no satisfactory general method for carrying out this conversion existed.

The N-acylhydrazines prepared by the present invention are useful as insecticides or pharmaceuticals such as anti-tuberculin agents. Hydrazines which can be made from N-acylhydrazines are useful as enzyme inhibitors, pharmaceuticals, insecticides, monoamine oxidase inhibitors, enzyme inhibitors, and anti-malarial agents. Amines prepared by the present invention are widely known to be useful as pharmaceuticals, agrichemicals, or insecticides.

The first step of the multistep sequence is the conversion of the prochiral keto group containing compound (1) to its prochiral N-acylhydrazone derivative (2) according to the following reaction:

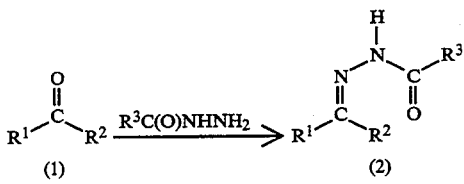

wherein
$R^1$ and $R^2$ are not the same and are each $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroalkyl; aryl; substituted aryl; aralkyl; ring substituted aralkyl; carboalkoxy; carboamido; acyl; vinyl; substituted vinyl, alkynyl; or $C(R^4)_2[C(R^4)_2]_qD[C(R^4)_2]_pR^4$;
D is O, S, $NR^4$, or $Si(R^4)_2$;
p and q are each integers, the same or different, from 1 to 8;
$R^3$ is aryl, substituted aryl, or a linear, branched or cyclic $C_1$ to $C_8$ alkyl; and
$R^4$ is each independently H; F; aryl; $C_1$ to $C_8$ alkyl; $C_1$ to $C_8$ fluoroalkyl; to $C_1$ to $C_8$ perfluoroalkyl; or $R^4$ together with $R^1$ or $R^2$ form a ring.

In this first step of the multistep process, and for all additional steps or processes described hereinafter, the substituents for substituted aryl for $R^3$ include hydrogen, halogen, alkyl, alkoxy, aryl, aryloxy, nitro, and amino. For $R^1$, $R^2$ and $R^4$, the substituents for substituted alkyl, substituted aryl, and ring substituted aralkyl are each independently hydrogen, halogen, alkyl, perfluoroalkyl, alkoxy, aryl, acyl, aryloxy, nitro, amino, carboalkoxy, trialkylsilyl, triphenylsilyl, vinyl, substituted vinyl and alkynyl.

Preferably, for purposes of economy for all processes herein, $R^3$ is phenyl, para-(methoxy)phenyl, or para-(dimethylamino)phenyl. Preferred $R^1$ and $R^2$ are 1) $R^1$ is phenyl and $R^2$ is methyl, ethyl, benzyl, or carbomethoxy; or 2) $R^1$ is para-(methoxy)phenyl, para-(carboethoxy)phenyl, para-(bromo)phenyl, para-(nitro)phenyl, 2-naphthyl, carboethoxy, carbomethoxy, or isopropyl, and $R^2$ is methyl. More preferred is when $R^1$ is carbomethoxy or carboethoxy and $R^2$ is phenyl or methyl, especially when $R^1$ is carbomethoxy or carboethoxy and $R^2$ is methyl, or when $R^1$ is phenyl and $R^2$ is carbomethoxy.

Particularly preferred combinations are wherein $R^1$ is phenyl, $R^2$ is methyl, and $R^3$ is phenyl, methyl, p-(nitro)phenyl, p-(methoxy)phenyl, p-(dimethylamino)phenyl, t-butoxy, or 2-furoyl; $R^1$ is p-(methoxy)phenyl, p-(trimethylsilyl)phenyl, p-(bromo)phenyl, p-(carboethoxy)phenyl, p-(nitro)phenyl, 2-naphthyl, tertbutoxy, or phenyl, $R^2$ is methyl, and $R^3$ is phenyl; $R^1$ is phenyl, $R^2$ is ethyl, benzyl, or trifluoromethyl, and $R^3$ is phenyl; $R^1$ is ethyl or isopropyl, $R^2$ is methyl, and $R^3$ is p-(dimethylamino)phenyl; $R^1$ is carbomethoxy, $R^2$ is phenyl, and $R^3$ is phenyl; $R^1$ is carboethoxy, $R^2$ is methyl, and $R^3$ is phenyl; $R^1$ is methyl, $R^2$ is carboethoxy, and $R^3$ is phenyl; or $R^1$ and $R^2$ together are 1-indanyl and $R^3$ is phenyl.

The N-acylhydrazone derivatives are prepared by a standard procedure as in "The Chemistry of the Amides", Patai. S.; Zabicky, J., Eds.; John Wiley and Sons: New York, N.Y., pp 560–561, (1970), which is herein incorporated by reference. This procedure involves treatment of a carboxylic acid hydrazide with a ketone in the presence of a catalytic amount of acid.

The present invention further comprises a process for the asymmetric hydrogenation of N-acylhydrazones. This process also constitutes the second step of the multistep process of the present invention. The catalytic asymmetric hydrogenation of a prochiral N-acylhydrazone derivative (2) to an optically active mixture of enantiomeric N-acylhydrazines (3A) and (3B) proceeds according to the following reaction:

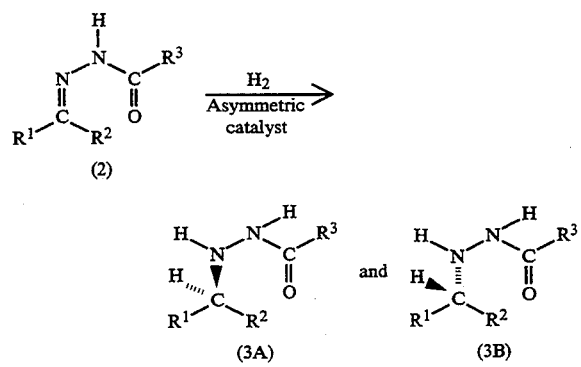

wherein
$R^1$, $R^2$ and $R^3$ are as previously defined.

This asymmetric hydrogenation is the key value-adding step of the multi-step process. Asymmetry is generated in the product by the action of the asymmetric catalyst.

This reduction is carried out in solvents such as toluene, tetrahydrofuran, dimethylformamide, dichloromethane, alcohols, water, or alcohol/water mixtures. Preferred are the organic solvents, more preferably alcohols and most preferably isopropanol.

The temperature range employed for the hydrogenation can range from about $-50°$ to about $100°$ C. A preferred range is from about $-10°$ to about $50°$ C. Most preferred temperature range is from $-10°$ to about $20°$ C. The time of reaction is typically 0.5 to 72 hours, more preferably 1 to 48 hours, depending upon reaction substrate and temperature.

The reaction is typically run under hydrogen, or hydrogen diluted by inert gas (e.g., nitrogen, argon)

atmosphere. Oxygen must be excluded from the reaction. Starting materials should preferably be free of oxygen.

Reaction pressure is typically 15 to 1500 psi (1 to 100 atmospheres, $1\times10^5$ to $1\times10^7$ pascals). The preferred pressure range is 15 to 60 psi (1 to 4 atmospheres, $1\times10^5$ to $4\times10^5$ pascals). It is preferred to carry out the hydrogenation reaction with vigorous agitation.

The product may be isolated by any of the techniques employed in synthetic organic chemistry. Evaporation of solvent, distillation, crystallization, filtration, and chromatographic methods may all be employed to advantage. N-acylhydrazines are useful as intermediates in the preparation of hydrazines and amines, and are also useful as pharmaceuticals.

Catalysts suitable for use herein comprise complexes wherein a transition metal is bonded to both phosphorus atoms of a group selected from one of the following:

(S)-(−)-2,2'-bis(diphenylphosphino)-1,1'-binaphthyl ((S)-BINAP);
(R)-(+)-2,2'-bis(diphenylphosphino)-1,1'-binaphthyl ((R)-BINAP);
(2S,4S)-2,4-bis(diphenylphosphino)pentane ((S,S)-SKEWPHOS);
(2R,4R)-2,4-bis(diphenylphosphino)pentane ((R,R)-SKEWPHOS);
(2S,3S)-bis(diphenylphosphino)butane ((S,S)-CHIRAPHOS);
(2R,3R)-bis(diphenylphosphino)butane ((R,R)-CHIRAPHOS);
(+)-2,3-O-isopropylidene-2,3-dihydroxy-1,4-bis(diphenylphosphino)butane ((+)-DIOP);
(−)-2,3-O-isopropylidene-2,3-dihydroxy-1,4-bis(diphenylphosphino)butane ((−)-DIOP);
phenyl-4,6-O-(R)-benzylidene-2,3-O-bis(diphenylphosphino)-β-D-glucopyranoside ((R)-GLUP);
phenyl-4,6-O-(S)-benzylidene-2,3-O-bis(diphenylphosphino)-β-D-glucopyranoside ((S)-GLUP);
a chiral ligand of formula I or II

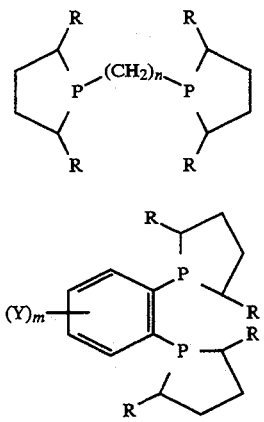

wherein
n is an integer from 1 to 12;
Y is each independently hydrogen, halogen, alkyl, alkoxy, aryl, aryloxy, nitro, dialkylamino, vinyl, substituted vinyl, alkynyl, of sulfonic acid;
m is an integer from 1 to 4;
R is a radical comprising linear, branched or cyclic $C_1$ to $C_8$ alkyl; linear, branched or cyclic $C_1$ to $C_8$ fluoroalkyl; linear, branched or cyclic $C_1$ to $C_8$ perfluoroalkyl; aryl; substituted aryl; aralkyl; ring-substituted aralkyl; or —$C(R^5)_2[C(R^5)_2]_qX[C(R^5)_2]_pR^5$;

X is O, S, $NR^6$, $PR^6$, $AsR^6$, $SbR^6$, divalent aryl, divalent fused aryl, divalent 6-membered ring heterocyclic group, divalent 5-membered ring heterocyclic group, or divalent fused heterocyclic group;
$R^5$ is each independently H; F; aryl; $C_1$ to $C_8$ alkyl; $C_1$ to $C_8$ fluoroalkyl; or $C_1$ to $C_8$ perfluoroalkyl; or where together $R^5$ and $R^6$ form a ring;
q and p are as defined above;
$R^6$ is hydrogen; $C_1$ to $C_8$ alkyl; $C_1$ to $C_8$ fluoroalkyl; $C_1$ to $C_8$ perfluoroaklyl; aryl; substituted aryl; aralkyl; ring substituted aralkyl; or $C(R^5)_2[C(R^5)_2]_qZ[C(R^5)_2]_pR^5$;

Z is O, S, $NR^5$, $PR^5$, $AsR^5$, or $SbR^5$;
$R^5$, p and q are as defined above, and
provided that the catalyst is other than ruthenium (2,2'-bis(diphenylphosphino)-1,1'-binaphthyl)dichloride dimer or bis-(2-methylallyl)ruthenium ((2S,5S)-2,5-dimethylphospholano)benzene.

For R and $R^6$, the substituents for aryl and ring substituted aralkyl include hydrogen, halogen, alkyl, alkoxy, aryl, aryloxy, nitro, amino, vinyl, substituted vinyl, alkynyl, or sulfonic acid.

The BINAP, SKEWPHOS, CHIRAPHOS, and DIOP ligand groups are commercially available as phosphines from many sources, including Strem Chemicals, 7 Mulliken Way, Newburyport, Mass. 01950. GLUP is prepared according to the procedure of R. Selke et al., *J. Mol. Cat.*, 37, 213 (1986). Chiral ligands of formula I are prepared as detailed in U.S. Pat. No. 5,008,457 of Burk, herein incorporated by reference, and chiral ligands of formulae I and II are prepared as detailed hereinafter.

The chiral ligands of formulae I and II are prepared by first reacting a bis(primary phosphine) with a strong base capable of deprotonating a P—H bond. Bases such as methyl lithium, n-butyl lithium, phenyl lithium, or lithium diisopropylamide, can be used to remove one proton from the phosphorus atom of each primary phosphine group, thereby creating an anion. This anion is then reacted with a cyclic sulfate of formula A to generate a carbon-phosphorus bond on each phosphorus. The addition of more strong base then removes the remaining proton from each phosphorus and subsequently creates a heterocyclic phospholane by formation of a second carbon-phosphorus bond through sulfate group displacement. The reaction is conducted in an organic solvent such as tetrahydrofuran, diethyl ether or dimethoxyethane at a temperature of from about 0° C. to the boiling point of the solvent employed. Reaction at about 20° C. to about 30° C. is preferred. An inert atmosphere is required, with nitrogen or argon being preferred. The reaction is conducted at ambient pressure.

More specifically, as in reaction Scheme A, deprotonation of 1,2-bis(phosphino)benzene (commercially available from Quantum Design, Inc., Austin, Tex.; 512-258-4174) in tetrahydrofuran is accomplished with n-butyllithium (2 equivalents) to give dilithium 1,2-bis(-phosphino)benzene. The resulting dianion is then reacted with a tetrahydrofuran solution of 1,4-diol cyclic sulfate of formula A (2 equivalents), followed after 1 hour, by the second addition of n-butyl lithium (2.2 to 2.3 equivalents). Standard workup procedures afford the pure products, 1,2-bis(phospholano)benzenes exemplified by formula II, in good yield (80–90%). In general, the crude products obtained through this procedure are analytically pure and no further purification steps (i.e. distillation) are required.

By using the commercially available 1,2-bis(phosphino)ethane (Quantum Design, Inc., Austin, Tex.; 512-258-4174), the bis(phospholano)ethanes of formula I as previously described in U.S. Pat. No. 5,008,457, also are readily prepared in high yield and in pure form by this route (Scheme A). The described synthesis appears only to be limited by the availability of the primary phosphine starting material, and can be easily applied to the preparation of other chiral ligands.

SCHEME A

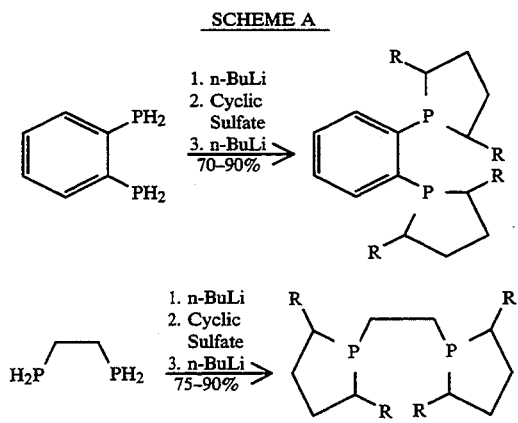

Cyclic sulfates suitable for use in preparation of the phospholanes are symmetric chiral 1,4-diol cyclic sulfates of formula A

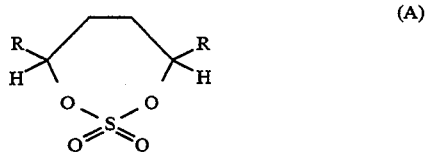

(A)

wherein

R is as previously defined for chiral ligands of formula I or II.

These cyclic sulfates are prepared from 1,4-diols, and are useful in the preparation of chiral ligands having a high degree of enantiomeric purity. An example of this preparative reaction is shown in Scheme B.

SCHEME B

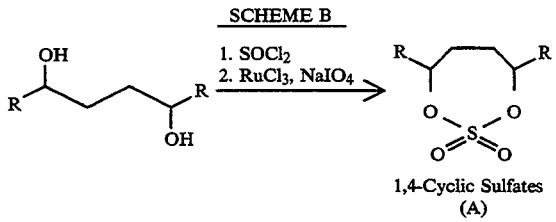

1,4-Cyclic Sulfates
(A)

The cyclic sulfates are prepared from chiral 1,4-diols which are prepared as in U.S. Pat. No. 5,021,131. The diols are reacted with thionyl chloride to afford the corresponding 1,4-diol cyclic sulfites (not isolated) which are subsequently oxidized to the crystalline products, symmetric 1,4-diol cyclic sulfates of formula A, by $NaIO_4$ and a catalytic amount of $RuCl_3$. The cyclic sulfates are then used in reaction with primary phosphines in the presence of strong base to prepare the chiral phospholane ligands I or II.

Preferred for use in the process of the present invention are cyclic sulfates having a high degree of enantiomeric purity. Also preferred processes are those wherein R for the cyclic sulfate and resulting ligands is methyl, ethyl, or isopropyl.

The ligands are complexed with a transition metal so that the metal is bonded to both phosphorus atoms of the ligands I or II. Such complexes are prepared by reacting the chiral ligand, such as I or II, with an appropriate precursor complex. Typical precursor transition metal complexes suitable for use herein include, among others, $[(COD)_2M]^+X^-$ wherein COD is 1,5-cyclooctadiene, M is rhodium or iridium, and X is $BF_4$, $SbF_6$, $PF_6$, or $CF_3SO_3$. The preparation is usually conducted in an organic solvent under an inert atmosphere such as nitrogen or argon. The reaction is conducted at ambient pressure at a temperature between 0° C. and the boiling point of the solvent. The resulting complexes containing the ligands, such as I or II, have a high degree of enantiomeric purity and are useful as catalysts which provide high enantiomeric selectivity in hydrogenation of unsaturated substrates.

The asymmetric catalysts can also be generated in situ by reacting the ligand with appropriate precursor complexes such as $[CODRhCl]_2$ or $[NBDRhCl]_2$ wherein COD is 1,5-cyclooctadiene and NBD is norbornadiene. Specific details of such a preparation are exemplified in Becalski et al., Inorg. Chem., 30, 5002–5008 (1991).

Preferred for use in the present invention are catalysts wherein the chiral ligand is of formula II complexed with a transition metal. Particularly preferred are catalysts wherein the chiral ligand is of formula II wherein R is methyl, ethyl or isopropyl, Y is hydrogen, and m is four. Preferred catalysts contain the transition metals rhodium or iridium. Especially preferred is rhodium. Specific preferred catalysts for use herein include:

[(COD)Rh(1,2-bis((2R,5R)-2,5-diethylphospholano)-benzene)]+$CF_3SO_3$− or the (2S,5S) analog thereof;

[(COD)Rh(1,2-bis((2R,5R)-2,5-diethylphospholano)ethane)]+$CF_3SO_3$− or the (2S,5S) analog thereof;

[(COD)Rh(1,2-bis((2S,5S)-2,5-dimethylphospholano)benzene)]+$CF_3SO_3$− or the (2R,5R) analog thereof;

[(COD)Rh(1,2-bis((2R,5R)-2,5-diisopropylphospholano)benzene)]+$CF_3SO_3$− or the (2S,5S) analog thereof; and

[(COD)Rh(1,2-bis((2R,5R)-2,5-diisopropylphospholano)ethane)]+$CF_3SO_3$− or the (2S,5S) analog thereof.

The present invention further comprises a process for the reductive N—N bond cleavage of N-acylhydrazines to amines. This process is the conversion of a N-acylhydrazine (3) to the corresponding amine (4) with the simultaneous generation of a carboxylic amide (5) according to the following reaction:

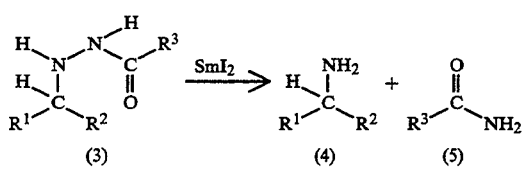

wherein

R¹, R² and R³ are as previously defined.

This process also constitutes the third step of the multistep process for the conversion of prochiral keto group-bearing compounds to chiral amino group-bearing compounds when the starting N-acylhydrazine is optically active.

An important facet of this aspect of the present invention is that optically active amines of formula (4A) and (4B) as previously defined can be prepared by starting with optically active mixture of enantiomeric N-acylhydrazines of formula (3A) and (3B) as previously defined. Any asymmetry of the starting material N-acylhydrazine is completely preserved, i.e., there is no racemization, in the product amine, when an optically active starting material is employed.

Samarium diiodide is purchased as a tetrahydrofuran solution from Alfa Products, P.O. Box 8247, Ward Hill, Mass. 01835-0747. A preferred mode of reaction is to add the samarium diiodide dissolved in tetrahydrofuran to an alcoholic (methanol or ethanol) solution of the N-acylhydrazine. The molar ratio of samarium diiodide to N-acylhydrazine employed is from about 2 to 5, preferably from about 2 to 3.

The temperature range employed for the samarium diiodide cleavage can range from 0° to about 50° C. A preferred range is from 0° to about 30° C. The most preferred temperature range is from 0° to about 20° C. The time of reaction is typically 0.25 to 3 hours, more preferably 0.25 to 1 hours. In some cases the reaction is practically instantaneous.

The reaction is typically run under an inert gas (e.g., nitrogen, argon) atmosphere. Oxygen should be excluded from the reaction. Starting materials should preferably be free of oxygen and preferably free of moisture.

The reaction is typically carried out at atmospheric pressure, but it is deemed possible to carry out the reaction at elevated or reduced pressures if desired. It is preferred to carry out the samarium diiodide cleavage reaction with vigorous agitation.

The product may be isolated by any of the techniques employed in organic synthetic chemistry. Evaporation of solvent, distillation, crystallization, filtration, chromatographic methods may all be employed to advantage.

The present invention further comprises an opitcally active N-acylhydrazine of formula (3A) or (3B), or a mixture thereof,

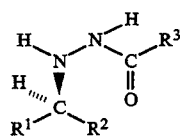

(3A)

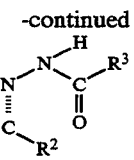

(3B)

wherein

R¹ and R² are not the same and are each $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroalkyl; aryl; substituted aryl; aralkyl; ring substituted aralkyl; carboalkoxy; carboamido; acyl; vinyl; substituted vinyl; alkynyl; or $C(R^4)_2[C(R^4)_2]_qD[C(R^4)_2]_pR^4$;

D is O, S, $NR^4$, or $Si(R^4)_2$;

p and q are each integers, the same or different, from 1 to 8;

$R^4$ is each independently H; F; aryl; $C_1$ to $C_8$ alkyl; $C_1$ to $C_8$ fluoroalkyl; to $C_1$ to $C_8$ perfluoroalkyl; or $R^4$ together with $R^1$ or $R^2$ form a ring; and R³ is aryl, substituted aryl, or a linear, branched or cyclic $C_1$ to $C_8$ alkyl.

Such optically active N-acylhydrazines are prepared from N-acylhydrazones according to step 2) of the multistep process previously described. Preferred are N-acylhydrazines of formula (3A) or (3B) wherein R¹ is phenyl, R² is methyl, and R³ is phenyl, methyl, p-(nitro)-phenyl, p-(methoxy)phenyl, p-(dimethylamino)phenyl, t-butoxy, or 2-furoyl; R¹ is p-(methoxy)phenyl, p-(trimethylsilyl)phenyl, p-(bromo)phenyl, p-(carboethoxy)phenyl, p-(nitro)phenyl, 2-naphthyl, tertbutoxy, or phenyl, R² is methyl, and R³ is phenyl; R¹ is phenyl, R² is ethyl, benzyl, or trifluoromethyl, and R³ is phenyl; R¹ is ethyl or isopropyl, R² is methyl, and R³ is p-(dimethylamino)phenyl; R¹ is carbomethoxy, R² is phenyl, and R³ is phenyl; R¹ is carboethoxy, R² is methyl, and R³ is phenyl; R¹ is methyl, R² is carboethoxy, and R³ is phenyl; or R¹ and R² together are 1-indanyl and R³ is phenyl.

In particular, preferred compounds are:
1-phenyl-1-(2-benzoylhydrazino)ethane;
1-p-methoxyphenyl-1-(2-benzoylhydrazino)ethane;
1-p-carboethoxyphenyl-1-(2-benzoylhydrazino)ethane;
1-p-nitrophenyl-1-(2-benozylhydrazino)ethane;
1-p-bromophenyl-1-(2-benzoylhydrazino)ethane;
1-phenyl-1-(2-benzoylhydrazino)propane;
1,2-diphenyl-1-(2-benzoylhydrazino)ethane;
1-(2-naphthyl)-1-(2-benzoylhydrazino)ethane;
ethyl 2-(2-benzoylhydrazino)propionate;
methyl 2-phenyl-2-(2-benzoylhydrazino)acetate;
3-methyl-2-(2-p-dimethylaminobenzoylhydrazino)butane;
1-phenyl-1-(2-p-methoxybenzoylhydrazino)ethane;
1-phenyl-1-(2-p-dimethylaminobenzoylhydrazino)ethane;
2-(2-p-dimethylaminobenzoylhydrazino)butane; or
1-phenyl-1-(2-benzoylhydrazino)-2,2,2-trifluoroethane.

EXAMPLES

General Procedures

All reactions and manipulations were performed in a nitrogen-filled Vacuum Atmospheres Dri-Lab glove-box or using standard Schlenk-type techniques. Benzene, toluene, diethyl ether ($Et_2O$), tetrahydrofuran (THF), glyme, hexane, and pentane were distilled from sodium-benzophenone ketyl under nitrogen. Methanol (MeOH) was distilled from Mg(OMe)$_2$. Other reagent grade alcohol solvents and water were simply purged with a stream of nitrogen for 30 min. prior to use.

Melting points were determined using a Mel-Temp apparatus in capillaries sealed under nitrogen and are uncorrected. HPLC analyses were performed using a Hewlett Packard Model HP 1090 LC interfaced to a HP 9000 Series 300 computer workstation. Optical Rotations were obtained using a Perkin Elmer Model 241 MC Polarimeter. NMR spectra were obtained on Nicolet NT-360 wide-bore (360 MHz $^1$H, 146 MHz $^{31}$P), Nicolet NMC-300 wide-bore (300 MHz $^1$H, 120.5 MHz $^{31}$P, 75.5 Mz $^{13}$C) and Nicolet QM-300 narrow-bore (300 MHz $^1$H) spectrometers. $^{13}$C and $^{31}$P NMR chemical shifts are positive downfield (and negative upfield) from external Me$_4$Si and 85% H$_3$PO$_4$, respectively. Elemental analyses were performed by Schwarzkopf Microanalytical Laboratory, Inc., Woodside, N.Y., or Pascher Mikroanalytisches Labor, Remagen-Bandorf (FRG).

The chemical names for the phosphines listed in the tables are given below. Each was purchased from Strem Chemicals (7 Mulliken Way, Newburyport, Mass. 01950) and used as received except for GLUP which was prepared by the procedure of R. Selke et al., *J. Mol. Cat.*, 37, 213 (1986).

(S)-BINAP is (S)-(−)-2,2'-Bis(diphenylphosphino)-1,1'-binaphthyl.

(R)-BINAP is (R)-(+)-2,2'-Bis(diphenylphosphino)-1,1'-binaphthyl.

(S,S)-SKEWPHOS is (2S,4S)-2,4-Bis(diphenylphosphino)pentane.

(R,R)-SKEWPHOS is (2R,4R)-2,4-Bis(diphenylphosphino)pentane.

(S,S)-CHIRAPHOS is (2S,3S)-Bis(diphenylphosphino)butane.

(R,R)-CHIRAPHOS is (2R,3R)-Bis(diphenylphosphino)butane.

(+)-DIOP is (+)-2,3-O-Isopropylidene-2,3-dihydroxy-1,4-bis(diphenylphosphino)butane.

(−)-DIOP is (−)2,3-O-Isopropylidene-2,3-dihydroxy-1,4-bis(diphenylphosphino)butane.

(R)-GLUP is Phenyl 4,6-O-(R)-benzylidene-2,3-O-bis(diphenylphosphino)-β-D-glucopyranoside.

(S)-GLUP is Phenyl 4,6-O-(S)-benzylidene-2,3-O-bis(diphenylphosphino)-β-D-glucopyranoside.

PREPARATION OF CATALYSTS HYDROXY ESTERS

Preparation of chiral β-hydroxy esters

The preparation of chiral β-hydroxy esters used in the diol syntheses was carried out as described by Noyori and coworkers who have reported the asymmetric reduction of β-keto esters using a ruthenium catalyst bearing the chiral phosphine ligand BINAP. All keto ester reductions were conducted on a 300 g scale in Hasteloy steel autoclave vessels in a MeOH/CH$_2$Cl$_2$ (300 mL/300mL) solvent mixture. The reactions were allowed to proceed at constant H$_2$ pressure (1500 psi) for 48 h at 25° C. Complete conversion of the β-keto ester substrates was observed in all cases and the products were simply distilled from the crude reaction mixture. Consistent with the results of Noyori et al., all products were determined >99% enantiomerically pure.

a) Preparation of chiral β-hydroxy acids

A mixture of (3R)-methyl 3-hydroxypentanoate (290 g, 2.2 mol) in water (200 mL) and ethanol (200 mL) was cooled to 0° C. To this cold solution was added a solution of KOH (185 g, 3.3 mol) in water (1 L). The reaction was then allowed to stir at 25° C. for 48 h. The resulting solution was concentrated to ca. 500 mL and acidified (conc. HCl) until pH=1 was reached. The precipitated salts were filtered and the filtrate was subjected to continuous liquid/liquid extraction with diethyl ether (1 L) for 24 h. The diethyl ether was removed on a rotovap to afford the product β-hydroxy acid as a colorless oil (250 g, 97%). The crude product was sufficiently pure to use in the next step (Kolbe-coupling).

b) Preparation of (2R,5R)-2,5-hexanediol

A 1000 mL jacketed reaction vessel is charged with (3R)-3-hydroxybutyric acid (52.0 g, 0.5 mol), methanol (390 mL) and sodium methoxide (110 mL of a 0.5N solution in methanol, 0.055 mol), and the mixture (pH=5.38) was cooled to 0° C. with a circulating bath. The electrode configuration used consists of a Pt foil anode (20 cm$^2$) wrapped around the outside bottom of a small jointed tube which fits inside a larger jointed tube with a Pt foil cathode (30 cm$^2$) lining the inside (avg electrode gap=2.5 mm). Using a 30 amp DC power supply (Hewlett Packard Model No. 6269B), a constant current (current density 0.25 A/cm$^2$) of 5 amp was applied until 56,000 coulombs (1.2 F/mol) were passed at which point complete conversion of hydroxy acid was indicated by gas chromatography. The reaction and gas evolution (H$_2$ and CO$_2$) proceed normally until ca. 1.0 F/mol current are passed, after which the resistance and solution pH are observed to increase. The colorless reaction mixture was then concentrated on a rotovap, and the resulting solid residue was extracted EtOAc (500 mL). After filtering, the remaining solids were stirred with EtOAc (100 mL) for 10 h, filtered, and the combined EtOAc extracts (600 mL) were concentrated to a colorless solid. The solids were dissolved in a minimum amount of warm Et$_2$O, quickly filtered through a coarse frit, and the filtrate cooled to −78° C. After two hours, the colorless crystals were filtered, washed with cold pentane, and dried in vacuo (Yield 14.4 g, 48%). mp 53°-54° C.; $[\alpha]^{25}_D = -39.6°\pm0.5°$ (c 1, CHCl$_3$) $^1$H NMR (CD$_2$Cl$_2$) δ1.15 (d, $J_{HH}$=6.2 Hz, 6H, CH$_3$), 1.50 (m, 4H, CH$_2$), 2.95 (br, 2H, OH), 3.75 (m, 2H, CH); $^{13}$C NMR (CD$_2$Cl$_2$) δ23.6, 35.9, 68.1. Anal. Calcd for C$_6$H$_{14}$O$_2$: C, 60.98; H, 11.94. Found: C, 61.12; H, 11.64.

c) Preparation of (2S,5S)-2,5-hexanediol

The titled compound was prepared as described above in b) except that (3S)-3-hydroxybutyric acid was used as substrate. $[\alpha]^{25}_D = +39.4°\pm0.5°$ (c 1, CHCl$_3$). Other spectroscopic properties were identical to those given for the (R,R) compound.

CYCLIC SULFATES

The cyclic sulfates are best stored at or below 0° C. as thermal decomposition was observed.

Preparation of (2R,5R)-2,5-hexanediol cyclic sulfate

To (2R,5R)-2,5-hexanediol (10.0 g, 0.085 mol) in CCl$_4$ (60 mL) was added via syringe thionyl chloride (7.75 mL, 0.106 mol). The resulting brownish solution was then refluxed for 1.5 h. After cooling to 25° C., the reaction was concentrated on a rotovap to afford a brown oil. The oil was then dissolved in a mixture of CCl4 (60 mL), CH3CN (60 mL), and H2O (90 mL) and the mixture was cooled to 0° C. To the cool mixture was added RuCl3 trihydrate (0.12 g, 0.58 mmol) followed by solid NaIO4 (36.2 g, 0.169 mol). The reaction was allowed to stir at 25° C. for 1 h. At this point, H2O (400 mL) was added and the mixture was extracted with diethyl ether (4×200 mL) and the combined ether extracts were washed with brine (2×100 mL). After drying over MgSO4 and filtration through a pad of SiO2 (important to remove dissolved Ru salts), the colorless solution was concentrated to ca. 20 mL on a rotovap. The addition of hexane (70 mL) and cooling to −10° C. afforded the product as a colorless crystalline solid which was filtered, washed with cold hexane and dried. Recrystallization from ether/hexane in a similar manner yielded pure colorless crystalline product which is best stored below 0° C. (12.4 g, 81%): mp 80° C. (dec.); $[\alpha]^{25}_D = -32.4°$ (c1. CHCl3); 1H NMR (CDCl3) δ1.32 (d, $J_{HH}$=6.5 Hz, 6H, CH3), 1.55 (m, 2H, CH2), 2.20 (m, 2H, CH2), 3.60 (m, 2H, CH); 13C NMR (CDCl3) δ22.67, 39.53, 44.31; HRMS (EI, direct insert): m/z 181.0551 (M++H, exact mass calcd for C6H13O4S: 181.0534), 137.0284 (M-C2H3O).

Preparation of (3S,6S)-2,5-octanediol cyclic sulfate

To (3S,6S)-2,5-octanediol (15.0 g, 0.103 mol) in CCl4 (60 mL) was added via syringe thionyl chloride (9.4 mL, 0.128 mol). The resulting brownish solution was then refluxed for 15 h. After cooling to 25° C., the reaction was concentrated on a rotovap to afford a brown oil. The oil was then dissolved in a mixture of CCl4 (90 mL), CH3CN (90 mL), and H2O (135 mL) and the mixture was cooled to 0° C. To the cool mixture was added RuCl3 trihydrate (0.18 g, 0.87 mmol) followed by solid NaIO4 (44.06 g, 0.206 mol). The reaction was allowed to stir at 25° C. for 1 h. At this point, H2O (500 mL) was added and the mixture was extracted with diethyl ether (4×200 mL) and the combined ether extracts were washed with brine (2×100 mL). After drying over MgSO4 and filtration through a pad of SiO2 (important to remove dissolved Ru salts), the colorless solution was concentrated to ca. 20 mL on a rotovap. The addition of hexane (70 mL) and cooling to −10° C. afforded the product as a colorless crystalline solid which was filtered, washed with cold hexane and dried. Recrystallization from ether/hexane in a similar manner yielded pure colorless crystalline product (1.5.1 g, 71%): mp 79.5°–80.5° C.; $[\alpha]^{25}_D = +28.6°$ (c1. CHCl3); 1H NMR (CDCl3) δ0.98 (t, $J_{HH}$=7.2 Hz, 6H, CH3), 1.5–1.75 (m, 6H, CH2), 2.20 (m, 2H, CH2), 3.35 (m, 2H, CH); 13C NMR (CDCl3) δ13.15, 30.62, 36.89, 51.34.

Preparation of (3S,6S)-3,6-dihydroxy-2,7-dimethyloctane cyclic sulfate

To (3S,6S)-3,6-dihydroxy-2,7-dimethyloctane (14.75 g, 0.085 mol) in CCl4 (60 mL) was added via syringe thionyl chloride (7.75 mL, 0.106 mol). The resulting pale yellow solution was then refluxed for 15 h. After cooling to 25° C., the reaction was concentrated on a rotovap to afford a pale yellow oil. The oil was then dissolved in a mixture of CCl4 (60 mL), CH3CN (60 mL), and H2O (90 mL) and the mixture was cooled to 0° C. To the cool mixture was added RuCl3 trihydrate (0.12 g, 0.58 mmol) followed by solid NaIO4 (36.2 g, 0.169 mol). The reaction was allowed to stir at 25° C. for 1 h. At this point, H2O (400 mL) was added and the mixture was extracted with diethyl ether (4×200 mL) and the combined ether extracts were washed with brine (2×100 mL). After drying over MgSO4 and filtration through a pad of SiO2 (important to remove dissolved Ru salts), the colorless solution was concentrated to dryness on a rotovap to afford a colorless crystalline material. Recrystallization from warm hexane (25 mL) and cooling to −10° C. afforded the product as a colorless crystalline solid which was filtered, washed with cold hexane and dried (18.14 g, 90%): mp 92.5°–93.5° C.; $[\alpha]^{25}_D = -55.0°$ (c1. CHCl3); 1H NMR (CDCl3) δ0.97 (d, $J_{HH}$=6.72 Hz, 6H, CH3), 0.98 (d, $J_{HH}$=6.66 Hz, 6H, CH3), 1.85 (m, 2H, CH), 1.90 (m, 4H, CH2), 4.40 (m, 2H, CH); 13C NMR (CDCl3) δ17.11, 18.67, 30.01, 32.79, 89.50.

PHOSPHINES

All reactions were conducted at room temperature (ca. 25° C.) unless otherwise noted.

Preparation of 1,2-Bis((2S,5S)-2,5-dimethylphospholano)benzene

To 1,2-bis(phosphino)benzene (0.79 g, 5.56 mmol) in THF (100 mL) was added dropwise via syringe n-BuLi (6.95 mL of a 1.6M solution in hexane, 2.0 equiv.). The yellow solution was allowed to stir for 1.5 h during which it became slightly cloudy. To the resulting mixture was then added a THF solution (10 mL) of (2R,5R)-2,5-hexanediol cyclic sulfate (2.03 g, 11.3 mmol) upon which the reaction decolorizes. After stirring for 1 h, n-BuLi (7.65 mL of a 1.6M hexane solution, 2.2 equiv.) is again added dropwise via syringe. Initially, a yellow color appeared and then faded, and a gelatinous precipitate formed (additional THF may be added at this point in order to maintain stirring). Toward the end of the addition the reaction remains yellow. The mixture was allowed to stir for 1.5 h, after which MeOH (3 mL) was added to quench any excess n-BuLi remaining. The resulting colorless mixture was filtered, and the gelatinous precipitate was washed thoroughly with diethyl ether. The filtrate was concentrated to produce a solid residue which was extracted with pentane (50 mL) and filtered. Concentration of the filtrate to 10 mL and cooling to −10° C. led to the product as colorless crystals (0.80 g) which were filtered and dried in vacuo. Further concentration of the filtrate and recrystallization of the residue from MeOH at −10° C. led to a second crop of crystals (0.53 g) which were filtered and dried in vacuo. Combined total yield 1.33 g (78%): $[\alpha]_D^{25} = +476°$ (c1, hexane); 1H NMR (C6D6) δ0.95 (ddd, 6H, CH3), 1.24 (ddd, 6H, CH3), 1.20–1.35 (m, 2H, CH2), 1.70 (m, 1H, CH2), 1.95 (m, 1H, CH2), 2.45 (m, 2H, CH), 7.05 (m, 2H, Ph), 7.25 (m, 2H, Ph); 31P NMR (C6D6) δ+2.9; 13C NMR (C6D6) δ18.65, 20.66 (t, $J_{CP}$=18.2 Hz, CH3), 32.89, 34.38 (t, $J_{CP}$=6.8 Hz), 35.91, 36.49, 128.0, 31.49, 144.56; HRMS (EI, direct insert): m/z 306.1638 (M+, exact mass calcd for C18H28P2: 306.1667), 223.0796 (M-C6H11), 192.1064 (M-C6H11P).

Preparation of 1,2-Bis((2R,5R)-2,5-diethylphospholano)benzene

To 1,2-bis(phosphino)benzene (1.01 g, 7.11 mmol) in THF (100 mL) was added dropwise via syringe n-BuLi (8.90 mL of a 1.6M solution in hexane, 2.0 equiv.). The yellow solution was allowed to stir for 1.5 h during which it became slightly cloudy. To the resulting mixture was then added a THF solution (10 mL) of (3S,6S)-2,5-octanediol cyclic sulfate (3.0 g, 14.4 mmol) upon which the reaction decolorizes. After stirring for 1 h, n-BuLi (9.80 mL of a 1.6M hexane solution, 2.2 equiv.) is again added dropwise via syringe. Initially, a yellow color appeared and then faded. Toward the end of the addition the reaction remains yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate afforded the product as a colorless oil (2.02 g, 78%). The crude product is essentially pure and may be used without any further purification. If further purification is desired, the product may be distilled in vacuo: $[\alpha]hd\ D^{25} = -265°$ (c1, hexane); $^1H$ NMR ($C_6D_6$) $\delta 0.85$ (m, 6H, $CH_3$), 0.80–0.90 (m, 2H, $CH_2$), 0.97 (t, $J_{HH}=7.3$ Hz, 6H, $CH_3$), 1.10–1.40 (m, 4H, $CH_2$), 1.50–1.80 (m, 6H, $CH_2$), 1.90 (m, 2H, CH), 2.00–2.20 (m, 4H, $CH_2$), 2.35 (m, 2H, CH), 7.06 (m, 2H, Ph), 7.31 (m, 2H, Ph); $^{31}P$ NMR ($C_6D_6$) $\delta -4.5$; $^{13}C$ NMR ($C_6D_6$) $\delta 13.99$, 14.11 (d, $J_{PC}=4.15$ Hz), 25.37, 28.80 (t, $J_{PC}=16.56$ Hz), 33.06, 33.37, 41.92, 42.34 (t, $J_{CP}=6.70$ Hz), 127.62, 132.25, 144.33; HRMS (EI, direct insert): m/z 362.2245 ($M^+$, exact mass calcd for $C_{22}H_{36}P_2$: 362.2292), 293.1570 ($M-C_5H_9$), 251.1086 ($M-C_8H_{15}$), 216.1193 ($M-C_{11}H_{14}$), 185.1395 ($M-C_{11}H_{14}P$).

Preparation of
1,2-Bis((2R,5R)-2,5-diisopropylphospholano)benzene

To 1,2-bis(phosphino)benzene (1.20 g, 8.44 mmol) in THF (100 mL) was added dropwise via syringe n-BuLi (10.6 mL of a 1.6M solution in hexane, 2.0 equiv.). The yellow solution was allowed to stir for 1.5 h during which it became slightly cloudy. To the resulting mixture was then added a THF solution (10 mL) of (3S,6S)-3,6-dihydroxy-2,7-dimethyloctane cyclic sulfate (4.01 g, 17.0 mmol) upon which the reaction decolorized. After stirring for 1 h, n-BuLi (12.15 mL of a 1.6M hexane solution, 2.2 equiv.) is again added dropwise via syringe. Initially, a yellow color appeared and then faded. Toward the end of the addition the reaction remains yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate afforded the product as a viscous colorless oil (2.47 g, 70%). The crude product was essentially pure and may be used without any further purification. Further purification, if desired, may be accomplished by distillation in vacuo: $[\alpha]_D^{25} = +59.6° \pm 1°$ (c1, hexane); $^1H$ NMR ($C_6D_6$) $\delta 0.65$ (d, $J_{HH}=6.4$ Hz, 6H, $CH_3$), 0.80–1.10 (m, 2H, $CH_2$), 1.03 (d, $J_{HH}=6.6$ Hz, 12H, $CH_3$), 1.10 (d, $J_{HH}=6.5$ Hz, 6H, $CH_3$), 1.20–1.65 (m, 6H, $CH_2$), 1.65–2.20 (m, 6H, CH, $CH_2$), 2.40 (m, 2H, CH), 7.00 (m, 2H, Ph), 7.40 (m, 2H, Ph); $^{31}P$ NMR ($C_6D_6$) $\delta -11.2$; HRMS (EI, direct insert): m/z 418.2916 ($M^+$, exact mass calcd for $C_{26}H_{44}P_2$: 418.2918), 403.2633 ($M-CH_3$), 375.2351 ($M-C_3H_7$), 279.1535 ($M-C_{10}H_{19}$), 247.1485 ($M-C_{10}H_{20}P$ fragment).

Preparation of
1,2-Bis((2R,5R)-2,5-diethylphospholano)ethane

To 1,2-bis(phosphino)ethane (0.667 g, 7.10 mmol) in THF (100 mL) was added via syringe n-BuLi (8.90 mL of a 1.6M solution in hexane, 2.0 equiv.). The pale yellow solution was allowed to stir for 1.5 h. To the resulting mixture was then added a THF solution (10 mL) of (3S,6S)-2,5-octanediol cyclic sulfate (3.0 g, 14.4 mmol) upon which the reaction decolorizes. After stirring for 1 h, n-BuLi (10.2 mL of a 1.6M hexane solution, 2.3 equiv.) is again added dropwise via syringe. Initially, a yellow color appeared and then faded, and a gelatinous precipitate formed (additional THF may be added at this point in order to maintain stirring). Toward the end of the addition the reaction remains pale yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate afforded the product as a colorless oil (1.92 g, 86%). The crude product is essentially pure and may be used without any further purification. If further purification is desired, the product may be distilled in vacuo: $[\alpha]_D^{25} = +320°$ (c1, hexane); $^1H$ NMR ($C_6D_6$) $\delta 0.93$ (t, $J_{HH}=8.2$ Hz, 6H, $CH_3$), 0.95–1.10 (m, 2H, $CH_2$), 1.03 (t, $J_{HH}=7.8$ Hz, 6H, $CH_3$), 1.15–1.40 (m, 6H, $CH_2$), 1.45–1.75 (m, 12H, $CH_2$), 1.80 (m, 2H, CH), 1.95 (m, 2H, CH); $^{31}P$ NMR ($C_6D_6$) $\delta -5.9$; $^{13}C$ NMR ($C_6D_6$) $\delta 14.75$, 15.00, 20.32, 23.48, 29.46, 34.13, 34.94, 43.08, 45.85; HRMS (EI, direct insert): m/z 314.2289 ($M^+$, exact mass calcd for $C_{18}H_{36}P_2$: 314.2292), 286.1949 ($M-C_2H_4$), 203.1099 ($M-C_8H_{15}$), 172.1372 ($M-C_8H_{15}P$), 144.1037 ($C_8H_{17}P$ fragments).

Preparation of
1,2-Bis((2R,5R)-2,5-diisopropylphospholano)ethane

To 1,2-bis(phosphino)ethane (0.50 g, 5.32 mmol) in THF (75 mL) was added via syringe n-BuLi (6.65 mL of a 1.6M solution in hexane, 2.0 equiv.). The pale yellow solution was allowed to stir for 1.5 h. To the resulting mixture then was added a THF solution (10 mL) of (3S,6S)-3,6-dihydroxy-2,7-dimethyloctane cyclic sulfate (2.53 g, 10.7 mmol) upon which the reaction decolorized. After stirring for 1 h, n-BuLi (7.64 mL of a 1.6M hexane solution, 2.3 equiv.) was again added dropwise via syringe. Initially, a yellow color appeared and then faded, and a gelatinous precipitate formed (additional THF may be added at this point in order to maintain stirring). Toward the end of the addition the reaction remained pale yellow. The mixture was allowed to stir for 1.5 h, after which MeOH (3 mL) was added to quench any excess n-BuLi remaining. The resulting colorless mixture was concentrated to produce a gelatinous residue which was extracted with pentane (150 mL) and filtered. Concentration of the filtrate to ca. 10 mL and cooling to $-20°$ C. provided the product as colorless crystals which were filtered and dried in vacuo (1.45 g, 74%). The crude product was analytically pure and may be used without any further purification. If further purification is desired, the product may be recrystallized from $Et_2O/MeOH$ at $-20°$ C. to provide 1c as colorless crystals: $[\alpha]_D^{25} = -264° \pm 320°$ (c1, hexane); $^1H$ NMR ($C_6D_6$) $\delta 0.84$ (d, $J_{HH}=6.4$ Hz, 6H, $CH_3$), 0.80–1.10 (m, 2H, $CH_2$), 0.95 (d, $J_{HH}=6.6$ Hz, 6H, $CH_3$), 1.09 (d, $J_{HH}=6.5$ Hz, 6H, $CH_3$), 1.10 (d, $J_{HH}=6.5$ Hz, 6H, $CH_3$), 1.20–1.45 (m, 4H, $CH_2$), 1.45–1.75 (m, 8H, CH, $CH_2$), 1.80–2.05 (m, 4H, CH); $^{31}P$ NMR ($C_6D_6$) $\delta -10.1$; $^{13}C$ NMR ($C_6D_6$) $\delta 20.27$, 20.36, 22.24, 22.81, 23.21, 24.52, 29.48, 32.84, 33.04, 50.32, 52.19; HRMS (EI, direct insert): m/z 370.2894 ($M^+$, exact mass calcd for $C_{22}H_{44}P_2$: 370.2918), 355.2603 ($M-CH_3$), 342.2634 ($M-C_2H_4$), 327.2336 ($M-C_3H_7$), 231.1241 (M-$C_{10}H_{19}$), 199.1611 (M-$C_{10}H_{20}P$ fragment), 172.1387 ($C_{12}H_{23}P$ fragment).

COMPLEXES

Rhodium complex [(COD)Rh(1,2-Bis((2R,5R)-2,5-diethylphospholano)ethane)]+$CF_3SO_3^-$ (Complex A)

To [(COD)$_2$Rh]+OTf$^-$ (0.149 g, 0.32 mmol, COD=1,5-cyclooctadiene, OTf=$CF_3SO_3$) in THF (10 mL) at 25° C. was added dropwise a solution of 1,2-Bis((2R,5R)-2,5-diethylphospholano)ethane (0.1 g, 0.32 mol) in THF (3 mL). The solution turned orange from yellow upon the phosphine addition. The reaction was allowed to stir for 15 min, and then Et$_2$O (30 mL) was slowly added to the solution to produce a small amount of brown oil. The orange solution was decanted from the oil. Further slow addition of Et$_2$O yielded a bright orange precipitate which was filtered and washed with Et$_2$O. The solids were dissolved in CH$_2$Cl$_2$ (5 mL), filtered, and Et$_2$O (30 mL) was added slowly to the orange filtrate to provide the product as a bright orange microcrystalline solid (0.125 g, 58%): $^1$H NMR (CD$_2$Cl$_2$) δ1.07 (t, $J_{HH}$=7.3 Hz, 6H, CH$_3$), 1.13 (t, $J_{HH}$=7.3 Hz, 6H, CH$_3$), 1.20–1.50 (m, 8H, CH$_2$), 1.50–2.10 (m, 12H, CH, CH$_2$), 2.15–2.60 (m, 12H, CH, CH$_2$), 4.85 (m (br), 2H, COD—CH), 5.30 (m (br), 2H, COD—CH), 7.70 (m, 4H, Ph); $^{31}$P NMR (CD$_2$Cl$_2$) δ71.2 (d, $J_{RhP}$=145.3 Hz); Anal. Calcd for C$_{27}$H$_{48}$F$_3$O$_3$P$_2$SRh: C, 48.07; H, 7.17; P, 9.18. Found: C, 48.19; H, 7.23; P, 9.15.

Rhodium complex [(COD)Rh(1,2-Bis((2R,5R)-2,5-diisopropyl-phospholano)ethane)]+$CF_3SO_3^-$ (Complex B)

This complex was prepared in a manner analogous to that described above with the exception that the diphospholane 1,2-Bis((2R,5R)-2,5-diisopropylphospholano)ethane was used. $^1$H NMR (CD$_2$Cl$_2$) δ0.97 (d, $J_{HH}$=6.6 Hz, 6H, CH$_3$), 0.90–1.20 (m, 2H, CH$_2$), 1.10 (d, $J_{HH}$=6.6 Hz, 6H, CH$_3$), 1.15 (d, $J_{HH}$=6.5 Hz, 6H, CH$_3$), 1.40 (d, $J_{HH}$=6.5 Hz, 6H, CH$_3$), 1.30–1.50 (m, 4H, CH$_2$), 1.50–2.00 (m, 10H, CH, CH$_2$), 2.00–2.60 (m, 12H, CH), 4.85 (m (br), 2H, COD—CH), 5.30 (m (br), 2H, COD—CH); $^{31}$P NMR (CD$_2$Cl$_2$) δ65.2 (d, $J_{RhP}$=145.2 Hz); Anal. Calcd for C$_{31}$H$_{56}$F$_3$O$_3$P$_2$SRh: C, 50.96; H, 7.72; P, 8.48. Found: C, 51.15; H, 7.71; P, 8.52.

Rhodium complex [(COD)Rh(1,2-Bis((2S,5S)-2,5-dimethyl-phospholano)benzene)]+$CF_3SO_3^-$ (Complex C)

This complex was prepared in a manner analogous to that described above with the exception that the diphospholane 1,2-Bis((2S,5S)-2,5-dimethylphospholano)benzene was used. $^1$H NMR (CD$_2$Cl$_2$) δ1.01 (dd, $J_{HH}$=6.8 Hz, $J_{PH}$=15.0 Hz, 6H, CH$_3$), 1.45 (dd, $J_{HH}$=7.1 Hz, $J_{PH}$=18.2 Hz, 6H, CH$_3$), 1.55 (m, 2H, CH$_2$), 1.95 (m, 2H, CH, CH$_2$), 2.20–2.60 (m, 12H, CH$_2$, CH), 2.65 (m, 2H, CH, CH$_2$), 2.75 (m, 2H, CH, CH$_2$), 5.05 (br, 2H, COD—CH), 5.62 (br, 2H, COD—CH), 7.75 (m, 4H, Ph); $^{31}$P NMR (CD$_2$Cl$_2$) δ76.3 (d, $J_{RhP}$=148.7 Hz); Anal. Calcd for C$_{27}$H$_{40}$F$_3$O$_3$P$_2$SRh: C, 48.66; H, 6.05; P, 9.29. Found: C, 48.43; H, 6.02; P, 9.31.

Rhodium complex [(COD)Rh(1,2-Bis((2R,5R)-2,5-diethyl-phospholano)benzene)]+$CF_3SO_3^-$ (Complex D)

To [(COD)$_2$Rh]+OTf$^-$ (0.13 g, 0.28 mmol, COD=1,5-cyclooctadiene, OTf=$CF_3SO_3$) in THF (10 mL) at 25° C. was added dropwise a solution of 1,2-Bis((2R,5R)-2,5-diethylphospholano)benzene (0.10 g, 0.28 mmol) in THF (5 mL). The solution turned orange from yellow upon the phosphine addition. The reaction was allowed to stir for 15 min, and then Et$_2$O (30 mL) was slowly added to the solution to produce an orange microcrystalline precipitate which was filtered, washed with Et$_2$O, and briefly dried. The solids were dissolved in CH$_2$Cl$_2$ (5 mL), filtered, and Et$_2$O (30 mL) was added slowly to the orange filtrate to provide the product as an orange microcrystalline solid (0.112 g, 56%): $^1$H NMR (CD$_2$Cl$_2$) δ0.86 (t, $J_{HH}$=7.3 Hz, 6H, CH$_3$), 1.02 (t, $J_{HH}$=7.3 Hz, 6H, CH$_3$), 1.2–1.6 (m, 6H, CH$_2$), 1.85 (m, 4H, CH, CH$_2$), 2.20 (m, 2H, CH, CH$_2$), 2.20–2.70 (m, 14H, CH$_2$, CH), 4.90 (m (br), 2H, COD—CH), 5.60 (m (br), 2H, COD—CH), 7.70 (m, 4H, Ph); $^{31}$P NMR (CD$_2$Cl$_2$) δ69.5 (d, $J_{RhP}$=148.3 Hz); Anal. Calcd for C$_{31}$H$_{48}$F$_3$O$_3$P$_2$SRh: C, 51.53; H, 6.69; P, 8.57. Found: C, 52.14; H, 6.72; P, 8.64.

Rhodium complex [(COD)Rh(1,2-Bis((2R,5R)-2,5-diisopropyl-phospholano)benzene)]+$CF_3SO_3^-$ (Complex E)

This complex was prepared in a manner analogous to that described above with the exception that the diphospholane 1,2-Bis((2R,5R)-2,5-diisopropylphospholano)benzene was used. $^1$H NMR (CD$_2$Cl$_2$) δ0.72 (d, $J_{HH}$=6.6 Hz, 6H, CH$_3$), 0.73 (d, $J_{HH}$=6.7 Hz, 6H, CH$_3$), 1.13 (d, $J_{HH}$=6.5 Hz, 6H, CH$_3$), 1.14 (d, $J_{HH}$=6.6 Hz, 6H, CH$_3$), 1.60 (m, 4H, CH$_2$), 1.95 (m, 4H, CH, CH$_2$), 2.15 (m, 2H, CH$_2$), 2.20–2.45 (m, 6H, CH$_2$, CH), 2.45–2.70 (m, 8H, CH, CH$_2$), 4.95 (br, 2H, COD—CH), 5.60 (br, 2H, COD—CH), 7.65 (m, 2H, Ph), 7.75 (m, 2H, Ph); $^{31}$P NMR (CD$_2$Cl$_2$) δ65.5 (d, $J_{RhP}$=148.5 Hz).

SUBSTRATES

N-Acylhydrazone Substrates

All substrates were prepared by the same general and standard procedure (see "The Chemistry of the Amides", Patai. S.; Zabicky, J., Eds.; John Wiley and Sons: New York, 1970, pp 560–561) involving treatment of a carboxylic acid hydrazide (commercially available from either Aldrich Chemical Co., P.O. Box 355, Milwaukee, Wis. 53021 or Lancaster Synthesis Inc., P.O. Box 1000, Windham, N.H. 03087-9977) in tetrahydrofuran solvent with a ketone in the presence of a catalytic amount of acid catalyst (3 drops concentrated HCl). In general, most products precipitated as colorless solids from the reaction solution. The solids were filtered, washed with tetrahydrofuran, diethyl ether, and pentane, and dried in vacuo. In cases were the product did not precipitate, the reaction was monitored by thin layer chromatography. Upon completion, the reaction was concentrated, and purified by crystallization or column chromatography on silica.

Acetophenone N-Benzoylhydrazone

To a solution of benzoic acid hydrazide (5.70 g, 0.042 mol) in tetrahydrofuran (75 mL) was added acetophenone (5.5 g, 0.046 mol) followed by concentrated. HCl (3 drops). The reaction was allowed to stir for 12 h at 25° C. during which time the product precipitated as a colorless crystalline solid. The product was filtered, washed with tetrahydrofuran (1×30 mL), diethyl ether (3×60 mL) and pentane (2×60 mL), and the crystalline solids were dried in vacuo (6.65 g, 64%). $^1$H NMR (CD$_2$Cl$_2$): δ2.35 (s, 3H, CH$_3$), 7.30–8.0 (m, 10H, Ph), 9.0 (br, 1H, NH). All other substrates were prepared in a similar fashion.

Asymmetric Hydrogenation of Hydrazones: General Procedure

In a nitrogen-filled dry box, a 100 mL Fisher-Porter tube was charged with substrate (0.4 to 1.26 mmol), followed by degassed solvent (10 to 20 mL, 0.04 to 0.063M in substrate), and catalyst (0.3 mol %). After six vacuum/H$_2$ cycles to purge the lines of air and two vacuum/H$_2$ cycles on the reaction mixture, the tube was pressurized to an initial pressure of 15 to 60 psig (1×10$^5$ to 4×10$^5$ pascals) H$_2$ (Matheson, 99.998%). The reactions were allowed to stir at temperatures ranging from −10° C. to 25° C. until no further hydrogen uptake was observed. Complete (100%) conversion to product was indicated by GC, TLC and $^1$H NMR analyses, unless otherwise noted. The reactions were concentrated, and the residue passed through a short SiO$_2$ column (EtOAC/hexane or Et$_2$O/pentane, 50/50) to remove catalyst residues. Without further purification, the enantiomeric excesses were determined directly with the crude products thus obtained.

EXAMPLE 1

Asymmetric Hydrogenation of Acetophenone N-Benzoylhydrazone

A 100 mL Fisher-Porter tube was charged with a stir bar, acetophenone N-benzoyhydrazone (300 mg, 1.26 mmol), 2-propanol (15 mL) and rhodium catalyst [(COD)Rh(1,2-Bis((2R,5R)-2,5-diethylphospholano)-benzene)]$^+$CF$_3$SO$_3^-$ (1.0 mg, 0.00136 mmol). While the substrate is not completely soluble in 2-propanol under these conditions, the reaction proceeds normally. The tube was then connected to a hydrogen tank (Matheson, 99.998%) and the lines were purged of air by four vacuum/H$_2$ cycles. After two vacuum/H$_2$ cycles on the reaction mixture, the tube was pressurized to an initial pressure of 60 psig (4×10$^5$ pascals) H$_2$ and the reaction tube was rapidly placed in a 0° C. bath. After allowing 20 min. for equilibration, the stirring was started and the reaction was allowed to proceed until no further hydrogen uptake was observed (12 h). At this point, the reaction was homogeneous. Complete conversion to product was indicated by thin layer chromatography and capillary gas chromatography (methyl silicone column). The reaction was concentrated on a rotovap and the residue was chromatographed on a short SiO$_2$ column (ca. 6×0.5 cm) using 50% ethyl acetate/hexane as eluent. The fractions containing product were concentrated on a rotovap to give (S)-(−)-1-phenyl-1-(2-benzoylhydrazino)ethane as a colorless crystalline solid (275 mg, 91%). Enantiomeric excess analysis by HPLC using the Daicel column Chiralcel OJ (90/10 hexane/2-propanol; 40° C., 0.5 mL/min flow) indicated product of 92% enantiomeric purity. The same reaction using the antipodal catalyst, [(COD)Rh(1,2-Bis((2S,5S)-2,5-diethylphospholano)-benzene)]$^+$CF$_3$SO$_3^-$, afforded the opposite enantiomer of the product, (R)-(+)-1-phenyl-1-(2-benzoylhydrazino)ethane, with identical enantiomeric excess (92%).

Samarium(II) Iodide-Induced N—N Bond Cleavage: General Procedure

To the hydrazone hydrogenation products in methanol was added rapidly dropwise a solution of samarium(II) iodide (2.2 mole equivalents, obtained as a tetrahydrofuran solution from Alfa Products, P.O. Box 8247, Ward Hill, Mass. 01835-0747). Upon addition, the blue color of the samarium(II) iodide solution decolorized. After complete addition, the reaction was allowed to stir for 30 min. The reaction was then concentrated on a rotovap, and to the resulting residue was added 1M HCl. The aqueous layer was extracted with diethyl ether to remove essentially all organic by-products. These combined fractions were discarded. The aqueous layer was made basic to litmus by the addition of 3M NaOH and then was extracted with diethyl ether. The combined ether extractions were dried over potassium carbonate or a small amount of magnesium sulfate. Concentration of the ether provided the amine as essentially the only product.

EXAMPLE 2

Samarium(II) Iodide-Induced N—N Bond Cleavage of 2-Phenyl-2-(2-benzoylhydrazino)ethane To (S)-(−)-2-phenyl-2-(2-benzoylhydrazino)ethane (0.40 g, 1.66 mmol, 89% ee) in methanol (7 mL) was added rapidly dropwise a solution of samarium(II) iodide (70 mL of a 0.05M solution in tetrahydrofuran). After complete addition, the reaction was allowed to stir for 30 min. The reaction was then concentrated on a rotovap, and to the resulting residue was added 1M HCl (15 mL). The aqueous layer was extracted with diethyl ether (8×25 mL). The aqueous layer was made basic to litmus by the addition of 3M NaOH and then was extracted with diethyl ether (8×25 mL). The combined ether extractions were dried over a small amount of magnesium sulfate. Concentration of the ether solution on a rotovap provided the product. (S)-(−)-α-methylbenzylamine as a colorless oil (0.144 g, 72%): $[\alpha]_D^{20} = -37.1°$ (c 1.33, C$_6$H$_6$), $^1$H NMR (CDCl$_3$): δ1.40 (d, J$_{HH}$=6.3 Hz, 3H, CH$_3$), 1.70 (br, 2H, NH), 4.14 (q, J$_{HH}$=6.3 Hz, 1H, CH), 7.25 (m, 1H, Ph), 7.45 (m, 4H, Ph). The enantiomeric purity of the amine product (S)-(−)-α-methylbenzylamine was determined to be 89% ee using chiral capillary GC methods (J & W Cyclodex B column, 80° C., isothermal, (R) t$_1$ 20.57 min; (S) t$_2$ 21.33 min).

EXAMPLES 3–7

In Table I, are shown the results of hydrogenations of various N-acylhydrazones [i.e., the conversion of compounds of the structure (2) to compounds of the structure (3)] using the general procedure described above with substrates, catalysts, and conditions as specified in the table. The various catalysts were employed at a mole ratio of 0.1 mol % relative to N-acylhydrazone and at an initial hydrogen pressure of 30 psi (2×10$^5$ pascals) with a 0.05–0.06M solution or slurry of substrate in methanol. Essentially identical results were obtained at 1 atm (1×10$^5$ pascal). Reaction time was 2 to 4 hours. Enantiomeric excesses were determined by chiral HPLC (Daicel Chiralcel OJ).

EXAMPLE 8

In Table II is shown results from the effect of solvent in the asymmetric hydrogenation of compounds of the structure (2) to compounds of the structure (3) using the general procedure described above. For all entries in the table, $R^1$ was phenyl, $R^2$ was methyl, and $R^3$ was phenyl in both structure (2) and (3). For all entries the catalyst employed was the rhodium complex [(COD)Rh(1,2-Bis((2R,5R)-2,5-diethyl-phospholano)-benzene)]$^+$CF$_3$SO$_3^-$ at a mole ratio of 0.2 mol % relative to N-acylhydrazone and at an initial hydrogen pressure of 60 psi (4 atm, $4 \times 10^5$ pascal) with a 0.05-0.06M solution or slurry of substrate in the chosen solvent. Reaction temperature was 20° C. Enantiomeric excesses were determined by chiral HPLC (Daicel Chiralcel OJ).

EXAMPLES 9-16

In Table III, are shown the results of additional hydrogenation experiments using the general procedure described above employing various catalysts. For all entries in the table, $R^1$ was phenyl, $R^2$ was methyl, and $R^3$ was phenyl in both structure (2) and (3). For entries 9-14 the catalyst was of the form [(COD)Rh(ligand)]$^+$CF$_3$SO$_3^-$. For entries 15-16 catalyst form was as shown. Catalysts were employed at a mole ratio of 0.5 mol % relative to N-acylhydrazone and at an initial hydrogen pressure of 60 psi (4 atm, $4 \times 10^5$ pascal) with a 0.05-0.06M solution or slurry of substrate in isopropanol. Reaction temperature was 20° C. Enantiomeric excesses were determined by chiral HPLC (Daicel Chiralcel OJ).

EXAMPLES 17-24

In Table IV are shown the results of additional hydrogenation experiments using the general procedure described above. For all entries in the table, $R^1$ was phenyl and $R^2$ was methyl in both structure (2) and (3). $R^3$ was as shown. For all entries the catalyst employed was the rhodium complex [(COD)Rh(1,2-Bis((2R,5R)-2,5-diethyl-phospholano)benzene)]$^+$CF$_3$SO$_3^-$ at a mole ratio of 0.5 mol % relative to N-acylhydrazone and at an initial hydrogen pressure of 30 psi (2 atm, $2 \times 10^5$ pascal) with a 0.05-0.06M solution or slurry of substrate in isopropanol. Reaction temperature was 20° C. Enantiomeric excesses were determined by chiral HPLC (Daicel Chiralcel OJ).

EXAMPLES 25-30

In Table V are shown the results of additional hydrogenation experiments using the general procedure described above. For all entries in the table, $R^1$ was para-X-C$_6$H$_4$-, X being as shown in the table, $R^2$ was methyl, and $R^3$ was phenyl in both structure (2) and (3). For all entries the catalyst employed was the rhodium complex [(COD)Rh(1,2-Bis((2R,5R)-2,5-diethylphospholano)-benzene)]$^+$CF$_3$SO$_3^-$ at a mole ratio of 0.5 mol % relative to N-acylhydrazone and at an initial hydrogen pressure of 60 psi (4 atm, $4 \times 10^5$ pascal) with a 0.05-0.06M solution or slurry of substrate in isopropanol. Reaction temperature was 20° C. Enantiomeric excesses were determined by chiral HPLC (Daicel Chiralcel OJ).

EXAMPLES 31-34

In Table VI are shown the results of additional hydrogenation experiments using the procedure and catalyst of Examples 25-30. For all entries $R^1$ was phenyl, $R^2$ was methyl and $R^3$ was phenyl in both structure (2) and (3). The reaction temperature was as listed. All other conditions were as in Examples 25-30.

EXAMPLES 35-50

In Table VII are shown the results of additional hydrogenation experiments. For all entries in the table, in both structure (2) and (3), $R^1$, $R^2$ and $R^3$ were as shown. For all entries the catalyst employed was the rhodium complex [(COD)Rh(1,2-Bis((2R,5R)-2,5-diethylphospholano)benzene)]$^+$CF$_3$SO$^-_3$ (except example 35 in which the 2S,5S analog was used), at a mole ratio of 0.2 mol % relative to N-acylhydrazone and at an initial hydrogen pressure of 60 psi (4 atm, $4 \times 10^5$ pascal) with a 0.05-0.06M solution or slurry of substrate in isopropanol. Reaction temperature and time was as shown in the table. Enantiomeric excesses were determined by chiral HPLC (Daicel Chiralcel OJ or OB).

Enantiomeric Excess Determinations

Enantiomeric excesses were determined for N-acylhydrazines of formula (3A) and (3B) by HPLC as follows: 1-phenyl-1-(2-benzoylhydrazino) ethane, Example 8, (HPLC, Daicel Chiralcel OJ, 40° C., 0.5 mL/min, 10% 2-propanol/90% hexane: (R) $t_1$ 15.6 min; (S) $t_2$ 18.5 min); 1-p-methoxyphenyl-1-(2-benzoylhydrazino)ethane, Example 36, (HPLC, Daicel Chiralcel OJ, 40° C., 0.75 mL/min, 10% 2-propanol/90% hexane: (R) $t_1$ 17.47 min; (S) $t_2$ 22.64 min); 1-p-carboethoxyphenyl-1-(2-benzoylhydrazino)ethane, Example 37, (HPLC, Daicel Chiralcel OJ, 40° C., 0.5 mL/min, 10% 2-propanol/90% hexane: (S) $t_1$ 33.08; (R) $t_2$ 37.39 min); 1-p-nitrophenyl-1-(2-benzoylhydrazino)ethane, Example 38, (HPLC, Daicel Chiralcel OJ, 40° C., 0.75 mL/min, 10% 2-propanol/90% hexane: (S) $t_1$ 41.38 min; (R) $t_2$ 48.55 min); 1-p-bromophenyl-1-(2-benzoylhydrazino)ethane, Example 39, (HPLC, Daicel Chiralcel OB, 40° C., 1.0 mL/min, 5% 2-propanol/95% hexane: (R) $t_1$ 12.75 min; (S) $t_2$ 20.55 min); 1-p-trimethylsilylphenyl-1-(2-benzoylhydrazino)ethane, Example 26, (HPLC, Daicel Chiralcel OJ, 40° C., 0.4 mL/min, 3% 2-propanol/97% hexane: (R) $t_1$ 23.06 min; (S) $t_2$ 25.47 min); 1-phenyl-1-(2-benzoylhydrazino)propane, Example 40, (HPLC, Daicel Chiralcel OB, 40° C., 0.5 mL/min, 5% 2-propanol/95% hexane: (R) $t_1$ 15.26 min; (S) $t_2$ 18.87 min); 1,2-diphenyl-1-(2-benzoylhydrazino)ethane, Example 41, (HPLC, Daicel Chiralcel OJ, 40° C., 0.5 mL/min, 10% 2-propanol/90% hexane: (S) $t_1$ 22.36 min; (R) $t_2$ 25.09 min); 1-(2-naphthyl)-1-(2-benzoylhydrazino)ethane, Example 43, (HPLC, Daicel Chiralcel OJ, 40° C., 1.0 mL/min, 10% 2-propanol/90% hexane: (R) $t_1$ 17.63 min; (S) $t_2$ 21.08 min); ethyl 2-(2-benzoylhydrazino)propionate, Example 44, (HPLC, Daicel Chiralcel OJ, 40° C., 0.5 mL/min, 10% 2-propanol/90% hexane: $t_1$ 13.55 min; $t_2$ 15.16 min); methyl 2-phenyl-2-(2-benzoylhydrazino)acetate, Example 45, (HPLC, Daicel Chiralcel OJ, 40° C., 0.5 mL/min, 10% 2-propanol/90% hexane: $t_1$ 27.35 min; $t_2$ 33.05 min); ethyl 3'methyl-2-(2-benzoylhydrazino)butyrate, Example 46, (HPLC, Daicel Chiralcel OJ, 40° C., 0.3 mL/min, 2% 2-propanol/98% hexane: $t_1$ 57.72 min; $t_2$ 61.39 min); 3,3-dimethyl-2-(2-benzoylhydrazino)butane, Example 49, (HPLC, Daicel Chiralcel OJ, 40° C., 0.5 mL/min, 10% 2-propanol/90% hexane: $t_1$ 10.45 min; $t_2$ 11.88 min); 1-phenyl-1-(2-p-nitrobenzoylhydrazino)ethane, Example 19, (HPLC, Daicel Chiralcel OJ, 40° C., 1.0 mL/min, 10% 2-propanol/90% hexane:

(S) t₁ 20.01 min; (R) t₂ 23.84 min); 1-phenyl-1-(2-p-methoxybenzoylhydrazino)ethane, Example 21, (HPLC, Daicel Chiralcel OJ, 40° C., 0.5 mL/min, 10% 2-propanol/90% hexane: (S) t₁ 25.46 min; (R) t₂ 27.77 min); 1-phenyl-1-(2-p-dimethylaminobenzoylhydrazino)ethane, Example 22, (HPLC, Daicel Chiralcel OJ, 40° C., 0.5 mL/min, 7.5% 2-propanol/92.5% hexane: (R) t₁ 46.70 min; (S) t₂ 48.97 min); 1-phenyl-1-(2-o-methoxybenzoylhydrazino)ethane, Example 20, (HPLC, Daicel Chiralcel OJ, 40° C., 0.4 mL/min, 10% 2-propanol/90% hexane: (R) t₁ 22.40 min; (S) t₂ 24.15 min); 3-methyl-2-(2-p-dimethylaminobenzoylhydrazino)butane, Example 47, (HPLC, Daicel Chiralcel OJ, 40° C., 0.5 mL/min, 10% 2-propanol/90% hexane: t₁ 16.61 min; t₂ 18.47 min); 2-(2-p-dimethylaminobenzoylhydrazino)butane, Example 48 (HPLC, Daicel Chiralcel OB, 40° C., 1.0 mL/min, 10% 2-propanol/90% hexane: t₁ 12.36 min; t₂ 22.40 min); 1-phenyl-1-(2-(2-furoyl)hydrazino)ethane, Example 24, (HPLC, Daicel Chiralcel OB, 40° C., 1.0 mL/min, 5% 2-propanol/95% hexane: (R) t₁ 12.10 min; (S) t₂ 15.60 min); 1-phenyl-1-(acetylhydrazino)ethane, Example 17, (GC, Chrompack, XE60-(S)-Val, 175° C. (isothermal) (S) t₁ 30.36 min; (R) t₂ 31.57 min); α-methylbenzylamine (GC, J&W Scientific, Cyclodex B, 80° C. (isothermal) (R) t₁ 20.57 min; (S) t₂ 21.33 min). Enantiomeric excesses listed are the average value obtained from 2-3 experiment s.

Optical Rotations-N-acylhydrazines of Formula (3A) and (3B)

(S)-1-phenyl-1-(2-benzoylhydrazino)ethane, Example 8, (92% ee; $[\alpha]_D^{20} = -163.6°$ (c 2.72, CHCl₃)); (S)-1-p-nitrophenyl-1-(2-benzoylhydrazino)ethane, Example 38, (97% ee; $[\alpha]_D^{20} = -211.8°$ (c 1, CHCl₃)); (S)-1-(2-naphthyl)-1-(2-benzoylhydrazino)ethane, Example 43, (95% ee; $[\alpha]_D^{20} = -204.5°$ (c 3.90, CHCl₃)); (S)-methyl 2-phenyl-2-(2-benzoylhydrazino)acetate, Example 45, (96% ee; $[\alpha]_D^{20} = -98.0°$ (c 1, CHCl₃)); (S)-ethyl 2-(2-benzoylhydrazino)propionate, Example 44, (88% ee; $[\alpha]_D^{20} = -57.4°$ (c 1, CHCl₃)); (S)-1-p-methoxyphenyl-1-(2-benzoylhydrazino)ethane, Example 36, (88% ee; $[\alpha]_D^{20} = -188.9°$ (c 0.67, CHCl₃)); (S)-1-p-carboethoxyphenyl-1-(2-benzoylhydrazino)ethane, Example 37, (96% ee; $[\alpha]_D^{20} = -200.0°$ (c 1, CHCl₃)); (S)-1-p-bromophenyl-1-(2-benzoylhydrazino)ethane, Example 39, (98% ee; $[\alpha]_D^{20} = -191.6°$ (c 1, CHCl₃)); (S)-1-phenyl-1-(2-p-methoxybenzoylhydrazino)ethane, Example 21, (96% ee; $[\alpha]_D^{20} = -163.6°$ (c 1, CHCl₃)); (S)-2-phenyl-2-(2-p-dimethylaminobenzoyl-hydrazino)ethane, Example 22, (92% ee; $[\alpha]_D^{20} = -150.4°$ (c 1, CHCl₃)); (S)-1-phenyl-1-(2-benzoylhydrazino)propane, Example 40, (84% ee; $[\alpha]_D^{20} = 31\ 132.2°$ (c 1, CHCl₃)); (S)-1,2-diphenyl-1-(2-benzoylhydrazino)ethane, Example 32, (84% ee; $[\alpha]_D^{20} = -79.8°$ (c 1, CHCl₃)); 3-methyl-2-(2-p-dimethylaminobenzoylhydrazino)butane, Example 47, (73% ee; $[\alpha]_D^{20} = +12.4°$ (c 1, CHCl₃)).

Absolute Configurations

The N-acylhydrazine (formula (3A) or (3B)) absolute configurations were established by converting to the primary amine (formula (4A) or (4B)) via the samarium-(II) iodide-induced N—N bond cleavage, followed by comparison of the sign of optical rotation of the amine with that of the authentic configurationally assigned compound. The following referenced compounds were used for comparison: (S)-(−)-α-methylbenzylamine ($[\alpha]_D^{20} = -40.3°$ (c 1.33, C₆H₆, commercial sample)); (R)-(+)-α-(2-naphthyl)ethylamine ($[\alpha]_D^{20} = +21.0°$ (c 2.0, ethanol)); (S)-(−)-α-ethylbenzylamine ($[\alpha]_D^{20} = -21.7°$ (c 1.0, benzene)); (R)-(+)-α-(p-methoxyphenyl)ethylamine ($[\alpha]_D^{20} = +21.6°$ (neat)); R-(−)-1,2-diphenylethylamine ($[\alpha]_D^{19} = -51.2°$ (c 3.7, ethanol)); (R)-(+)-α-(p-nitrophenyl)ethylamine (($[\alpha]_D^{20} = +16.7°$ (neat)).

¹H NMR Data for N-Acylhydrazines of Formula (3A) or (3B)

Example 8 1-phenyl-1-(2-benzoylhydrazino)ethane ¹H NMR (CDCl₃) d 1.50 (d, $J_{HH}=6.7$ Hz, 3H, CH₃), 4.37 (q, $J_{HH}=6.7$ Hz, 1H, NCH), 7.2–7.6 (m, 8H, Ph), 7.7 (m, 2H, Ph)

36 1-p-methoxyphenyl-1-(2-benzoylhydrazino)ethane ¹H NMR (CDCl₃) d 1.43 (d, $J_{HH}=6.6$ Hz, 3H, CH₃), 3.80 (s, 3H, OCH₃), 4.24 (q, $J_{HH}=6.6$ Hz, 1H, NCH), 6.85 (d, $J_{HH}=8.7$ Hz, 2H, Ph), 7.20–7.55 (m, 5H, Ph), 7.67 (d, $J_{HH}=8.7$ Hz, 2H, Ph)

37 1-p-carboethoxyphenyl-1-(2-benzoylhydrazino)ethane ¹H NMR (CDCl₃) d 1.38 (t, $J_{HH}=7.15$ Hz, 3H, CH₃), 1.45 (d, $J_{HH}=6.65$ Hz, 3H, CH₃), 4.35 (q, $J_{HH}=7.15$ Hz, 2H, CH₂), 4.38 (q, $J_{HH}=6.65$ Hz, 1H, NCH), 7.35–7.55 (m, 5H, Ph), 7.68 (d, $J_{HH}=8.6$ Hz, 2H, Ph), 8.02 (d, $J_{HH}=8.6$ Hz, 2H, Ph)

38 1-p-nitrophenyl-1-(2-benzoylhydrazino)ethane ¹H NMR (CDCl₃) d 1.47 (d, $J_{HH}=6.7$ Hz, 3H, CH₃), 4.46 (q, $J_{HH}=6.7$ Hz, 1H, NCH), 7.35–7.65 (m, 7H, Ph), 8.08 (m, 2H, Ph)

39 1-p-bromophenyl-1-(2-benzoylhydrazino)ethane ¹H NMR (CDCl₃) d 1.48 (d, $J_{HH}=6.7$ Hz, 3H, CH₃), 4.36 (q, $J_{HH}=6.7$ Hz, 1H, NCH), 7.25–7.55 (m, 7H, Ph), 7.67 (m, 2H, Ph)

40 1-phenyl-1-(2-benzoylhydrazino)propane ¹H NMR (CDCl₃) d 0.85 (t (dd), $J_{HH}=7.45$ Hz, 3H, CH₃), 1.79 (m, 1H, CH₂), 1.95 (m, 1H, CH₂), 4.06 (dd, $J_{HH}=8.76, 5.42$ Hz, 1H, NCH), 7.25–7.55 (m, 8H, Ph), 7.65 (m, 2H, Ph).

41 1,2-diphenyl-1-(2-benzoylhydrazino)ethane ¹H NMR (CDCl₃) d 3.13 (m, 2H, CH₂), 4.06 (dd, $J_{HH}=7.3$ Hz, 1H, NCH), 7.15–7.80 (m, 15H, Ph)

Example 43 1-(2-naphthyl)-1-(2-benzoylhydrazino)ethane ¹H NMR (CDCl₃) d 1.52 (d, $J_{HH}=6.62$ Hz, 3H, CH₃), 4.45 (q, $J_{HH}=6.62$ Hz, 1H, NCH), 7.3–7.9 (m, 7H, Ar)

44 ethyl 2-(2-benzoylhydrazino)propionate ¹H NMR (CDCl₃) d 1.26 (t, $J_{HH}=7.15$ Hz, 3H, CH₃), 1.40 (d, $J_{HH}=7.04$ Hz, 3H, CH₃), 3.87 (q, $J_{HH}7.04$ Hz, 1H, NCH), 4.18 (m, 2H, OCH₂), 7.40–7.60 (m, 3H, Ph), 7.72 (m, 2H, Ph)

45 methyl 2-phenyl-2-(2-benzoylhydrazino)acetate ¹H NMR (CDCl₃) d 3.75 (s, 3H, OCH₃), 5.01 (s, 1H, NCH), 7.35–7.8 (m, 10H, Ph)

47 3-methyl-2-(2-p-dimethylaminobenzoylhydrazino)butane ¹H NMR (CDCl₃) d 0.98 (d, $J_{HH}=6.15$ Hz, 3H, CH₃), 1.10 (d, $J_{HH}=6.73$ Hz, 3H, CH₃),·1.21 (d, $J_{HH}=6.70$ Hz, CH₃), 2.12 (m, 1H, CH), 3.03 (s, 6H, NCH₃), 3.34 (dq, $J_{HH}=6.63, 4.89$ Hz, 1H, NCH), 6.62 (d, $J_{HH}=8.75$ Hz, 2H, Ph), 7.84 (d, $J_{HH}=8.75$ Hz, 2H, Ph)

21 1-phenyl-1-(2-p-methoxybenzoylhydrazino)ethane ¹H NMR (CDCl₃) d 1.48 (d, $J_{HH}=6.6$ Hz, 3H, CH₃), 3.80 (s, 3H, OCH₃), 4.27 (q, $J_{HH}=6.6$ Hz, 1H, NCH), 6.88 (d, $J_{HH}=8.7$ Hz, 2H, Ph), 7.20–7.55 (m, 5H, Ph), 7.69 (d, $J_{HH}=8.7$ Hz, 2H, Ph)

22 1-phenyl-1-(2-p-dimethylaminobenzoylhydrazino)ethane ¹H NMR (CDCl₃) d 1.50 (d, $J_{HH}=6.7$ Hz, 3H, CH₃), 3.00 (s, 3H, NCH₃), 4.34 (q, $J_{HH}=6.7$ Hz, 1H, NCH), 6.65 (d, $J_{HH}$=8.85 Hz, 2H, Ph), 7.20–7.55 (m, 5H, Ph), 7.64 (d, $J_{HH}$=8.85 Hz, 2H, Ph)

Example 48  2-(2-p-dimethylaminobenzoylhydrazino)butane  
$^1$H NMR (CDCl$_3$) d 0.95 (t, $J_{HH}$=7.48 Hz, 3H, CH$_3$), 1.11 (d, $J_{HH}$=6.40 Hz, 3H, CH$_3$), 1.45 (m, 1H, CH$_2$), 1.68 (m, 1H, CH$_2$), 3.01 (s, 6H, NCH$_3$), 3.11 (m, 1H, NCH), 6.65 (d, $J_{HH}$=9.02 Hz, 2H, Ph), 7.72 (d, $J_{HH}$=9.02 Hz, 2H, Ph)

42  1-phenyl-1-(2-benzoylhydrazino)-2,2,2-trifluoroethane $^1$H NMR (CDCl$_3$) d 4.63 (q, $J_{HF}$=7.21 Hz, 1H, NCH), 7.30–7.85 (m, 10H, Ph)

TABLE I
Asymmetric N-acylhydrazone Hydrogenations: Ligand Variation (2)

$$\underset{R^1\;\;\;R^2}{C}=N-\underset{H}{N}-\underset{O}{\overset{\|}{C}}-R^3$$

| | | % ee | | |
|---|---|---|---|---|
| Example | Catalyst Complex | $R^1$ = Ph $R^2$ = Me $R^3$ = Ph | $R^1$ = Ph $R^2$ = Me $R^3$ = Me | $R^1$ = Me $R^2$ = CO$_2$Et $R^3$ = Ph |
| 3 | A | 63 | — | — |
| 4 | B | 30 | — | — |
| 5 | C | 61 | 40 | 77 |
| 6 | D | 72 | 53 | 78 |
| 7 | E | 64 | 40 | 60 |

Ph = phenyl  
CO$_2$Et = carboethoxy  
Me = methyl

TABLE II
Solvent Effects in Asymmetric Hydrogenation

| Solvent | % ee |
|---|---|
| Toluene/CH$_2$Cl$_2$ (4/1) | 7 |
| Tetrahydrofuran | 31 |
| N,N-dimethylformamide | 51 |
| CH$_2$Cl$_2$ | 53 |
| CH$_3$OH/H$_2$O (1/1) | 59 |
| CH$_3$OH | 72 |
| CH$_3$CH$_2$OH | 79 |
| CH$_3$CHOHCH$_3$ | 88 |
| 3-Pentanol | 82 |
| CF$_3$CH$_2$OH | 69 |

TABLE III
Asymmetric Hydrogenation Employing Various Catalysts

| Example | Ligand/Complex | % ee |
|---|---|---|
| 9 | D (100% conv. in 2 h) | 88 |
| 10 | (S,S)-SKEWPHOS | 9 |
| 11 | (S)-BINAP (75% conv. in 48 h) | 20 |
| 12 | (S,S)-CHIRAPHOS | 23 |
| 13 | (+)-DIOP | 20 |
| 14 | (R)-GLUP (40–% conv. in 60 h) | 17 |
| 15 | (CODRhCl)$_2$/1,2-bis(2R,5R)-2,5-diethylphospholano)benzene (in situ) | 64 |
| 16 | (CODRhCl)$_2$/(S,S)-CHIRAPHOS (in situ) | 40 |

TABLE IV
Asymmetric Hydrogenation With Various $R^3$ Substituents

| Example | $R^3$ | % ee |
|---|---|---|
| 17 | CH$_3$ | 53 |
| 18 | C$_6$H$_5$ | 88 |
| 19 | p-NO$_2$C$_6$H$_4$ | 24 |
| 20 | o-CH$_3$OC$_6$H$_4$ | 58 |
| 21 | p-CH$_3$OC$_6$H$_4$ | 91 |
| 22 | p-(CH$_3$)$_2$NC$_6$H$_4$ | 92 |
| 23 | t-Butoxy | 15 |
| 24 | 2-Furoyl | 76 |

TABLE V
Asymmetric Hydrogenation With Various X Substituents

| Example | X | % ee |
|---|---|---|
| 25 | OCH$_3$ | 79 |
| 26 | Si(CH$_3$)$_3$ | 84 |
| 27 | H | 88 |
| 28 | Br | 92 |
| 29 | CO$_2$CH$_2$CH$_3$ | 93 |
| 30 | NO$_2$ | 93 |

TABLE VI
Asymmetric N-benzoylhydrazone Hydrogenations: Temperature Effect $$\underset{C_6H_5\;\;\;Me}{C}=N-\underset{H}{N}-\underset{O}{\overset{\|}{C}}-C_6H_5$$

| Examples | Temperature (°C.) | Time (h) | % ee |
|---|---|---|---|
| 31 | 50 | 2 | 78 |
| 32 | 20 | 2 | 88 |
| 33 | 0 | 12 | 92 |
| 34 | −10 | 24 | 95 |

TABLE VII
Rhodium-Catalyzed Asymmetric Hydrogenation of N-Acylhydrazones (2)

$$\underset{R^1\;\;\;R^2}{C}=N-\underset{H}{N}-\underset{O}{\overset{\|}{C}}-R^3$$

| Example | $R^1$ | $R^2$ | $R^3$ | Temp. (°C.) | Time (h) | % ee, confign |
|---|---|---|---|---|---|---|
| 21 | C$_6$H$_5$ | CH$_3$ | p-CH$_3$OC$_6$H$_4$ | 20 | 2 | 91 (S) |
| 22 | C$_6$H$_5$ | CH$_3$ | p-(CH$_3$)$_2$NC$_6$H$_4$ | 20 | 2 | 92 (S) |
| 32 | C$_6$H$_5$ | CH$_3$ | C$_6$H$_5$ | 20 | 2 | 88 (S) |
| 33 | C$_6$H$_5$ | CH$_3$ | C$_6$H$_5$ | 0 | 12 | 92 (S) |
| 34 | C$_6$H$_5$ | CH$_3$ | C$_6$H$_5$ | −10 | 24 | 95 (S) |
| 35 | C$_6$H$_5$ | CH$_3$ | C$_6$H$_5$ | 0 | 12 | 92 (R) |
| 36 | p-CH$_3$OC$_6$H$_5$ | CH$_3$ | C$_6$H$_5$ | 0 | 24 | 88 (S) |
| 37 | p-CH$_3$CH$_2$O$_2$CC$_6$H$_4$ | CH$_3$ | C$_6$H$_5$ | 0 | 12 | 96 |
| 38 | p-NO$_2$C$_6$H$_4$ | CH$_3$ | C$_6$H$_5$ | 0 | 12 | 97 |

TABLE VII-continued

Rhodium-Catalyzed Asymmetric Hydrogenation of N-Acylhydrazones

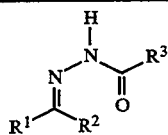

(2)

| Example | $R^1$ | $R^2$ | $R^3$ | Temp. (°C.) | Time (h) | % ee, config |
|---|---|---|---|---|---|---|
| 39 | p-BrC$_6$H$_4$ | CH$_3$ | C$_6$H$_5$ | 0 | 12 | 96 |
| 40 | C$_6$H$_5$ | CH$_3$CH$_2$ | C$_6$H$_5$ | −10 | 24 | 85 (S) |
| 41 | C$_6$H$_5$ | CH$_2$C$_6$H$_5$ | C$_6$H$_5$ | −10 | 36 | 84 (S) |
| 42 | C$_6$H$_5$ | CF$_3$ | C$_6$H$_5$ | 20 | 3 | 51 |
| 43 | 2-Naphthyl | CH$_3$ | C$_6$H$_5$ | 0 | 12 | 95 (S) |
| 44 | CO$_2$CH$_2$CH$_3$ | CH$_3$ | C$_6$H$_5$ | 0 | 24 | 90 |
| 45 | CO$_2$CH$_3$ | C$_6$H$_5$ | C$_6$H$_5$ | 20 | 36 | 91 |
| 46 | CO$_2$CH$_2$CH$_3$ | CH(CH$_3$)$_2$ | C$_6$H$_5$ | 20 | 10 | 55 |
| 47 | CH(CH$_3$)$_2$ | CH$_3$ | p-(CH$_3$)$_2$NC$_6$H$_4$ | −10 | 36 | 73 |
| 48 | CH$_2$CH$_3$ | CH$_3$ | p-(CH$_3$)$_2$NC$_6$H$_4$ | −10 | 24 | 43 |
| 49 | C(CH$_3$)$_3$ | CH$_3$ | C$_6$H$_5$ | 20 | 36 | 45 |
| 50 | $R^1$ and $R^2$ together are | | C$_6$H$_5$ | 20 | 72 | 33 |

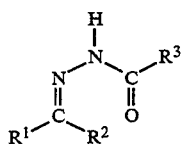

What is claimed is:
1. A process for the asymmetric hydrogenation of N-acylhydrazones comprising reacting with hydrogen a compound of formula 2

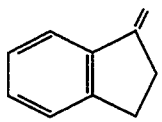

(2)

wherein
$R^1$ and $R^2$ are not the same and are each $C(R^4)_2[C(R^4)_2]_qD[C(R^4)_2]_pR^4$;
D is O, S, NR$^4$, or Si(R$^4$)$_2$;
p and q are each integers, the same of different, from 1 to 8;
$R^4$ is each independently H; F; aryl; C$_1$ to C$_8$ alkyl; C$_1$ to C$_8$ fluoroalkyl; to C$_1$ to C$_8$ perfluoroalkyl; or R$^4$ together with R$^1$ or R$^2$ form a ring; and
$R^3$ is aryl, aryl substituted with at least one of hydrogen, halogen, alkyl, alkoxy, aryl, aryloxy, nitro or amino, or a linear, branched or cyclic C$_1$ to C$_8$ alkyl;
in the presence of a catalyst comprising a complex wherein a transition metal is bonded to both phosphorus atoms of a chiral ligand selected from the group consisting of:
(S)-(−)-2,2′-bis(diphenylphosphino)-1,1′-binaphthyl;
(R)-(+)-2,2′-bis(diphenylphosphino)-1,1′-binaphthyl;
(2S,4S)-2,4-bis(diphenylphosphino)pentane;
(2R,4R)-2,4-bis(diphenylphosphino)pentane;
(2S,3S)-bis(diphenylphosphino)butane;
(2R,3R)-bis(diphenylphosphino)butane;
(+)-2,3-O-isopropylidene-2,3-dihydroxy-1,4-bis(diphenylphosphino)butane;
(−)-2,3-O-isopropylidene-2,3-dihydroxy-1,4-bis(diphenylphosphino)butane;
phenyl-4,6-O-(R)-benzylidene-2,3-O-bis(diphenylphosphino)-β-D-glucopyranoside;
phenyl-4,6-O-(S)-benzylidene-2,3-O-bis(diphenylphosphino)-β-D-glucopyranoside;
a chiral ligand of formula I and II

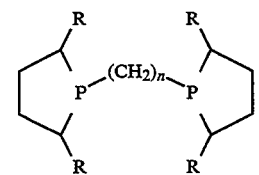

(I)

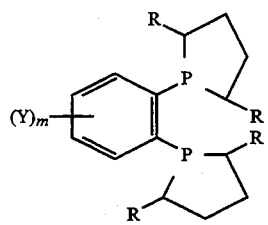

(II)

wherein
n is an integer from 1 to 12;
Y is each independently hydrogen, halogen, alkyl, alkoxy, aryl, aryloxy, nitro, dialkylamino, vinyl, substituted vinyl, alkynyl, of sulfonic acid;
m is an integer from 1 to 4;
R is a radical comprising linear, branched or cyclic C$_1$ to C$_8$ alkyl; linear, branched or cyclic C$_1$ to C$_8$ fluoroalkyl; linear, branched or cyclic C$_1$ to C$_8$ perfluoroalkyl; aryl; aryl substituted with at least one of hydrogen, halogen, alkyl, alkoxy, aryl, aryloxy, nitro, amino, vinyl, alkynyl, or sulfonic acid; aralkyl; ring-substituted aralkyl substituted with at least one hydrogen, halogen, alkyl, alkoxy, aryl, aryloxy, nitro, amino, vinyl, alkynyl, or sulfonic acid; and
provided that the catalyst is other than ruthenium (2,2′-bis(diphenylphosphino)-1,1′-binaphthyl)dichloride dimer or bis-2-(methylallyl)ruthenium ((2S,5S)-2,5-dimethylphospholano)benzene;

to yield an optically active mixture of enantomeric N-acylhydrazines of formula (3A) and (3B)

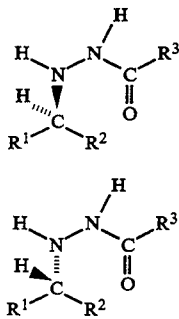

wherein
$R^1$, $R^2$ and $R^3$ are as defined above; and
wherein the compound of formula (3) exhibits optical activity to the extent of from greater than or equal to about 5% enantiomeric excess to at least about 50% enantiomeric excess.

2. The process of claim 1 wherein the compound of formula (3) exhibits optical activity to the extent of greater than or equal to about 50% enantiomeric excess.

3. The process of claim 1 wherein the compound of formula (3) exhibits optical activity to the extent of greater than or equal to about 90% enantiomeric excess.

4. A process for the conversion of prochiral keto group-bearing compounds to chiral amino group-bearing compounds comprising
Step 1) reacting a ketone of formula $R^1C(O)R^2$ with a carboxylic acid hydrazide of formula $R^3C(O)NHNH_2$ in the presence of an acid catalyst to generate an N-acylhydrazone of formula (2)

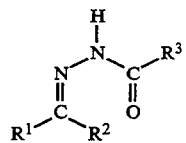

wherein
$R^1$ and $R^2$ are not the same and are each $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroalkyl; aryl; substituted aryl; aralkyl; ring substituted aralkyl; carboalkoxy; carboamido; acyl; vinyl; substituted vinyl; alkynyl; or $C(R^4)_2[C(R^4)_2]_qD[C(R^4)_2]_pR^4$;
D is O, S, $NR^4$, or $Si(R^4)_2$;
p and q are each integers, the same or different, from 1 to 8;
$R^4$ is each independently H; F; aryl; $C_1$ to $C_8$ alkyl; $C_1$ to $C_8$ fluoroalkyl; to $C_1$ to $C_8$ perfluoroalkyl; or $R^4$ together with $R^1$ or $R^2$ form a ring; and
$R^3$ is aryl, substituted aryl, or a linear, branched or cyclic $C_1$ to $C_8$ alkyl;
Step 2) reacting the N-acylhydrazone of formula (2) with hydrogen in the presence of a catalyst comprising a complex wherein a transition metal is bonded to both phosphorus atoms of a chiral ligand selected from the group consisting of:
(S)-(−)-2,2′-bis(diphenylphosphino)-1,1′-binaphthyl;
(R)-(+)-2,2′-bis(diphenylphosphino)-1,1′-binaphthyl;
(2S,4S)-2,4-bis(diphenylphosphino)pentane;
(2R,4R)-2,4-bis(diphenylphosphino)pentane;
(2S,3S)-bis(diphenylphosphino)butane;
(2R,3R)-bis(diphenylphosphino)butane;
(+)-2,3-O-isopropylidene-2,3-dihydroxy-1,4-bis(-diphenylphosphino)butane;
(−)-2,3-O-isopropylidene-2,3-dihydroxy-1,4-bis(-diphenylphosphino)butane;
phenyl-4,6-O-(R)-benzylidene-2,3-O-bis(diphenylphosphino)-β-D-glucopyranoside;
phenyl-4,6-O-(S)-benzylidene-2,3-O-bis(diphenylphosphino)-β-D-glucopyranoside;
chiral ligand of formula I and II

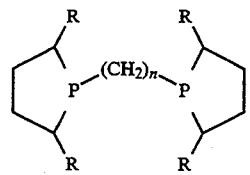

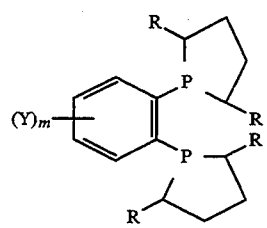

wherein
n is an integer from 1 to 12;
Y is each independently hydrogen, halogen, alkyl, alkoxy, aryl, aryloxy, nitro, dialkylamino, vinyl, substituted vinyl, alkynyl, of sulfonic acid;
m is an integer from 1 to 4;
R is a radical comprising linear, branched or cyclic $C_1$ to $C_8$ alkyl; linear, branched or cyclic $C_1$ to $C_8$ fluoroalkyl; linear, branched or cyclic $C_1$ to $C_8$ perfluoroalkyl; aryl; substituted aryl; aralkyl; ring-substituted aralkyl; and
provided that the catalyst is other than ruthenium (2,2′-bis(diphenylphosphino)-1,1′-binaphthyl)dichloride dimer or bis-(2-methylallyl)ruthenium ((2S,5S)-2,5-dimethylphospholano)benzene;
to yield an optically active mixture of enantiomeric N-acylhydrazines of formula (3A) and (3B)

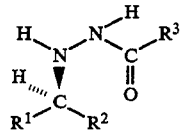

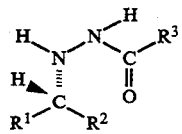

wherein
$R^1$, $R^2$ and $R^3$ are as previously defined; and
Step 3) reacting the optically active N-acylhydrazine of formula (3A) and (3B) with samarium diiodide to yield a carboxylic amide of formula $R^3C(O)NH_2$ and an optically active mixture of enantiomeric amines of formula (4A) and (4B)

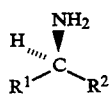 (4A)

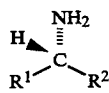 (4B)

wherein $R^1$, $R^2$, and $R^3$ are as previously defined, and wherein the amine exhibits optical activity to the extent of from greater than or equal to about 5% enantiomeric excess to at least about 50% enantiomeric excess.

5. The process of claim 4 wherein the amine exhibits optical activity to the extent of greater than or equal to about 50% enantiomeric excess.

6. The process of claim 4 wherein the amine exhibits optical activity to the extent of greater than or equal to about 90% enantiomeric excess.

7. The process of claim 1 or 4 wherein the catalyst is a complex of a transition metal rhodium or iridium and a chiral ligand of formula I or II.

8. The process of claim 7 wherein the catalyst is a complex of a transition metal rhodium or iridium and a chiral ligand of formula I or II wherein the ligand has an R group that is methyl, ethyl or isopropyl.

9. The process of claim 8 wherein the catalyst is [(COD)Rh(1,2-bis((2R,5R)-2,5-diethylphospholano)-benzene)]$^+$CF$_3$SO$_3^-$ or the (2S,5S) analog thereof;

[(COD)Rh(1,2-bis((2R,5R)-2,5-diethylphospholano)ethane)]$^+$CF$_3$SO$_3^-$ or the (2S,5S) analog thereof;

[(COD)Rh(1,2-bis((2S,5S)-2,5-dimethylphospholano)benzene)]$^+$CF$_3$SO$_3^-$ or the (2R,5R) analog thereof;

[(COD)Rh(1,2-bis((2R,5R)-2,5-diisopropylphospholano)benzene)]$^+$CF$_3$SO$_3^-$ or the (2S,5S) analog thereof; or

[(COD)Rh(1,2-bis((2R,5R)-2,5-diisopropylphospholano)ethane)]$^+$CF$_3$SO$_3^-$ or the (2S,5S) analog thereof.

10. The process of claim 1 or 4 wherein $R^1$ is phenyl and $R^2$ is carbomethoxy; or $R^1$ is carbomethoxy or carboethoxy and $R^2$ is methyl.

11. The process of claim 1 or 4 wherein $R^3$ is phenyl, para-(methoxy)phenyl, or para-(dimethylamino)phenyl.

12. The process of claim 1 or step 2) of claim 4 conducted in a solvent of isopropanol.

13. The process of claim 4, wherein step 3 is conducted in a solvent of tetrahydrofuran.

14. The process of claim 1 or step 2) of claim 4 conducted at a temperature of from about −50° C. to about 100° C.

15. A process for the preparation of amines comprising reacting the N-acylhydrazine of formula (3)

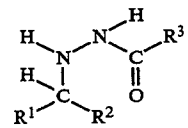 (3)

wherein $R^1$ and $R^2$ are the same or different and are each hydrogen, $C_1$ to $C_{15}$ cyclic, linear or branched alkyl; $C_1$ to $C_{15}$ cyclic, linear or branched substituted alkyl; $C_1$ to $C_8$ fluoroalkyl; $C_1$ to $C_8$ perfluoroakyl; aryl; substituted aryl; aralkyl; ring substituted aralkyl; carboalkoxy; carboamido; acyl; vinyl; substituted vinyl; alkynyl; or $C(R^4)_2[C(R^4)_2]_qD[C(R^4)_2]_pR^4$;

D is O, S, $NR^4$, or $Si(R^4)_2$;

p and q are each integers, the same or different, from 1 to 8;

$R^4$ is H; F; aryl; $C_1$ to $C_8$ alkyl; $C_1$ to $C_8$ fluoroalkyl; $C_1$ to $C_8$ perfluoroakyl; or $R^4$ together with $R^1$ or $R^2$ form a ring, and $R^3$ is aryl, substituted aryl, or a linear, branched or cyclic $C_1$ to $C_8$ alkyl; with samarium diiodide to reductively cleave the nitrogen-nitrogen bond to generate a carboxylic amide of formula $R^3C(O)NH_2$ and an amine of formula (4)

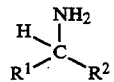 (4)

wherein $R^1$, $R^2$, and $R^3$ are as previously defined and the N-acylhydrazine and the amine each exhibit optical activity to the extent of greater than or equal to about 50% enantiomeric excess.

16. The process of claim 15 wherein the N-acylhydrazine and the amine exhibits optical activity to the extent of greater than or equal to about 90% enantiomeric excess.

17. The process of claim 15 wherein $R^1$ and $R^3$ are phenyl and $R^2$ is methyl or wherein $R^1$ is 2-naphthyl, $R^2$ is methyl and $R^3$ is phenyl.

* * * * *